(12) United States Patent
Woodard, Jr. et al.

(10) Patent No.: US 9,445,808 B2
(45) Date of Patent: Sep. 20, 2016

(54) ELECTROSURGICAL END EFFECTOR WITH TISSUE TACKING FEATURES

(71) Applicant: Ethicon Endo-Surgery, Inc., Cincinnati, OH (US)

(72) Inventors: James A. Woodard, Jr., Mason, OH (US); Kreena B. Modi, Akron, OH (US); Gary W. Knight, West Chester, OH (US); Andrew C. Yoo, Cincinnati, OH (US); Taylor W. Aronhalt, Loveland, OH (US); Joseph E. Young, Loveland, OH (US); Chester O. Baxter, III, Loveland, OH (US); Frederick E. Shelton, IV, Hillsboro, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 710 days.

(21) Appl. No.: 13/710,931

(22) Filed: Dec. 11, 2012

(65) Prior Publication Data
US 2014/0158741 A1 Jun. 12, 2014

(51) Int. Cl.
*A61B 17/068* (2006.01)
*A61B 17/04* (2006.01)
*A61B 17/072* (2006.01)
*A61B 18/14* (2006.01)
*A61B 17/06* (2006.01)

(52) U.S. Cl.
CPC ......... *A61B 17/068* (2013.01); *A61B 17/0401* (2013.01); *A61B 17/072* (2013.01); *A61B 17/07207* (2013.01); *A61B 17/07292* (2013.01); *A61B 18/1445* (2013.01); *A61B 2017/0409* (2013.01); *A61B 2017/0419* (2013.01); *A61B 2017/06052* (2013.01); *A61B 2017/0688* (2013.01); *A61B 2017/07228* (2013.01); *A61B 2017/07271* (2013.01); *A61B 2017/07278* (2013.01); *A61B 2017/07285* (2013.01); *A61B 2018/1455* (2013.01)

(58) Field of Classification Search
CPC .................. A61B 17/0401; A61B 2017/0409; A61B 17/068; A61B 17/072; A61B 2017/0419; A61B 2017/07278; A61B 2017/07271; A61B 2017/07228; A61B 17/07292; A61B 2018/1455
USPC ....................................... 227/175.1
See application file for complete search history.

(56) References Cited

U.S. PATENT DOCUMENTS

| | | | |
|---|---|---|---|
| 6,488,196 B1 * | 12/2002 | Fenton, Jr. | .................. 227/175.1 |
| 6,500,176 B1 | 12/2002 | Truckai et al. | |
| 6,783,524 B2 | 8/2004 | Anderson et al. | |
| 7,112,201 B2 | 9/2006 | Truckai et al. | |
| 7,125,409 B2 | 10/2006 | Truckai et al. | |

(Continued)

OTHER PUBLICATIONS

U.S. Appl. No. 61/410,603, filed Nov. 5, 2010.

*Primary Examiner* — Robert Long
*Assistant Examiner* — Xavier A Madison
(74) *Attorney, Agent, or Firm* — Frost Brown Todd LLC

(57) ABSTRACT

An apparatus is provided for operating on tissue. The apparatus includes an end effector having an upper jaw and lower jaw. The upper and lower jaws each include an electrode surface. The apparatus also includes a tissue tacking cartridge coupled to one of either the upper jaw or the lower jaw. The tissue tacking cartridge includes at least one fastener positioned outside of the electrode surfaces. The fastener is operable to be deployed from the tissue tacking cartridge. A tack loading cartridge may also be operable to load the end effector with at least one fastener.

20 Claims, 24 Drawing Sheets

(56) References Cited

U.S. PATENT DOCUMENTS

| | | |
|---|---|---|
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,381,209 B2 | 6/2008 | Truckai et al. |
| 7,708,180 B2 | 5/2010 | Murray et al. |
| 2004/0073256 A1* | 4/2004 | Marchitto et al. .......... 606/219 |
| 2007/0102472 A1* | 5/2007 | Shelton, IV ............... 227/175.1 |
| 2010/0292691 A1* | 11/2010 | Brogna .............. A61B 18/1445 606/45 |
| 2011/0087218 A1 | 4/2011 | Boudreaux et al. |
| 2011/0248064 A1* | 10/2011 | Marczyk ....................... 227/114 |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078248 A1 | 3/2012 | Worrell et al. |
| 2012/0116379 A1 | 5/2012 | Yates et al. |
| 2013/0023868 A1 | 1/2013 | Worrell et al. |
| 2013/0030428 A1 | 1/2013 | Worrell et al. |

* cited by examiner

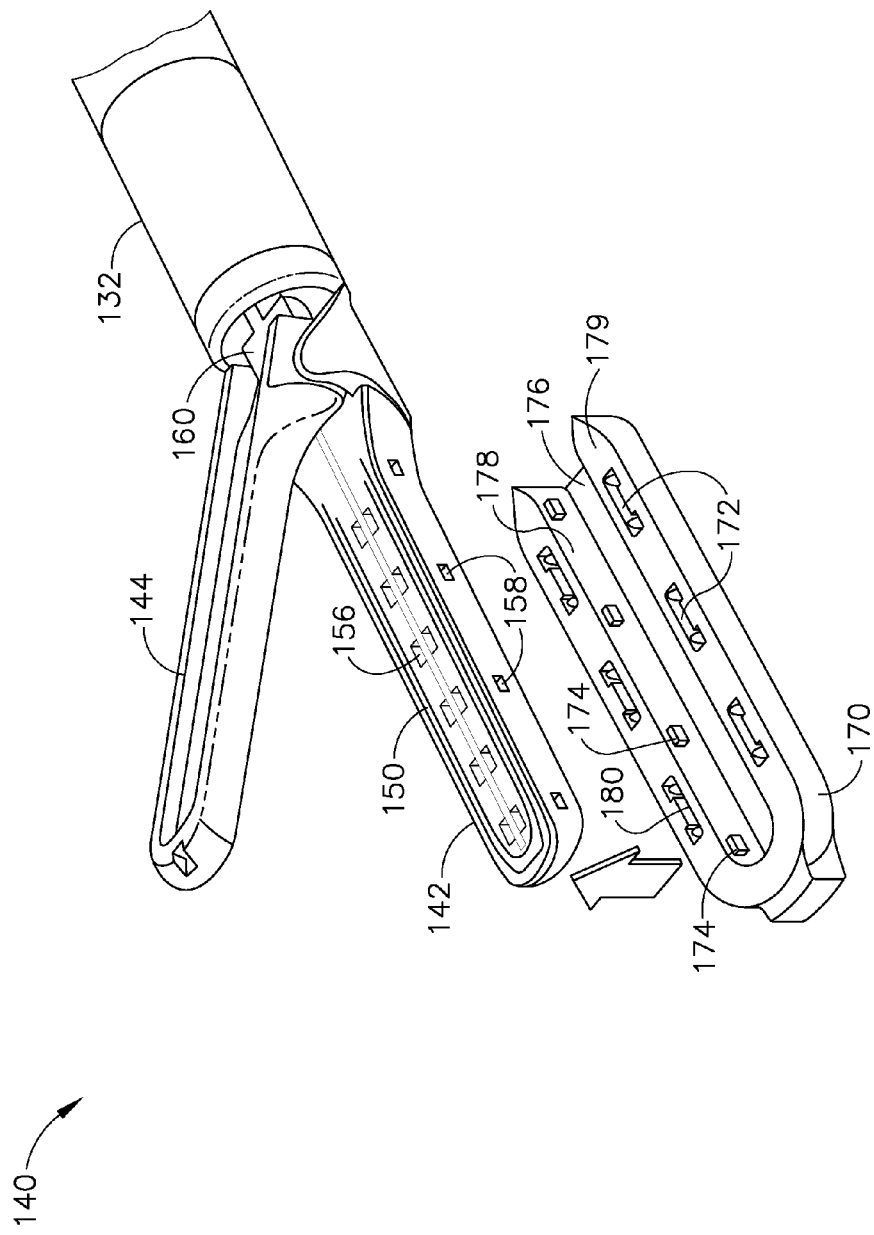

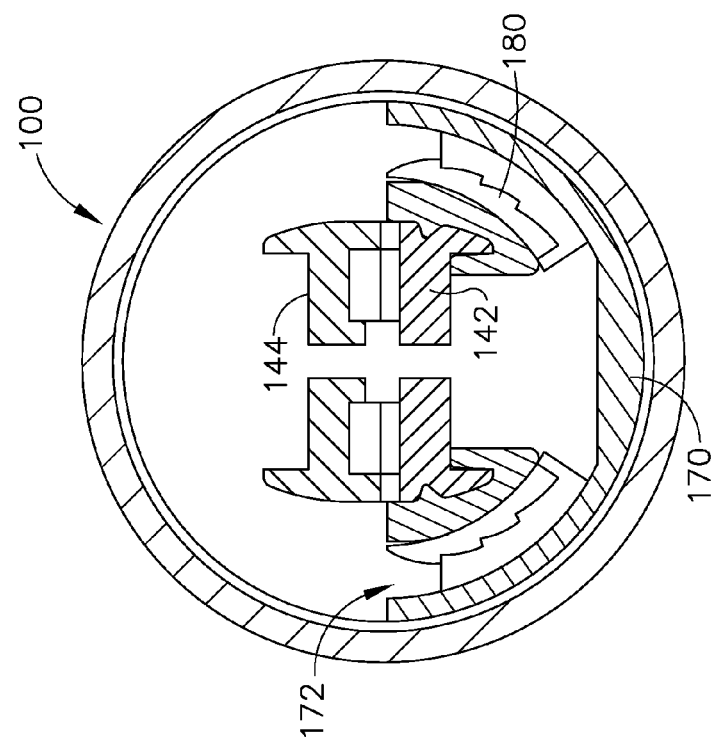
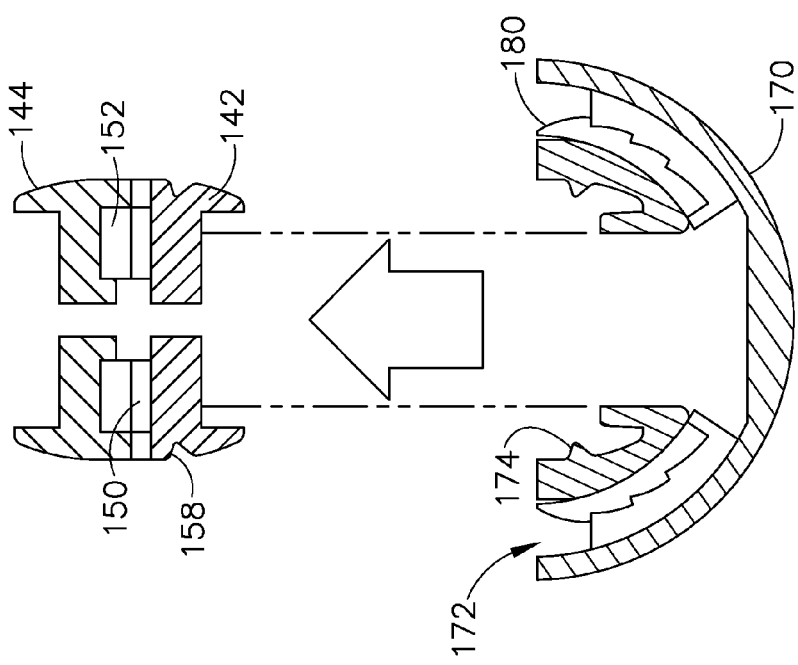

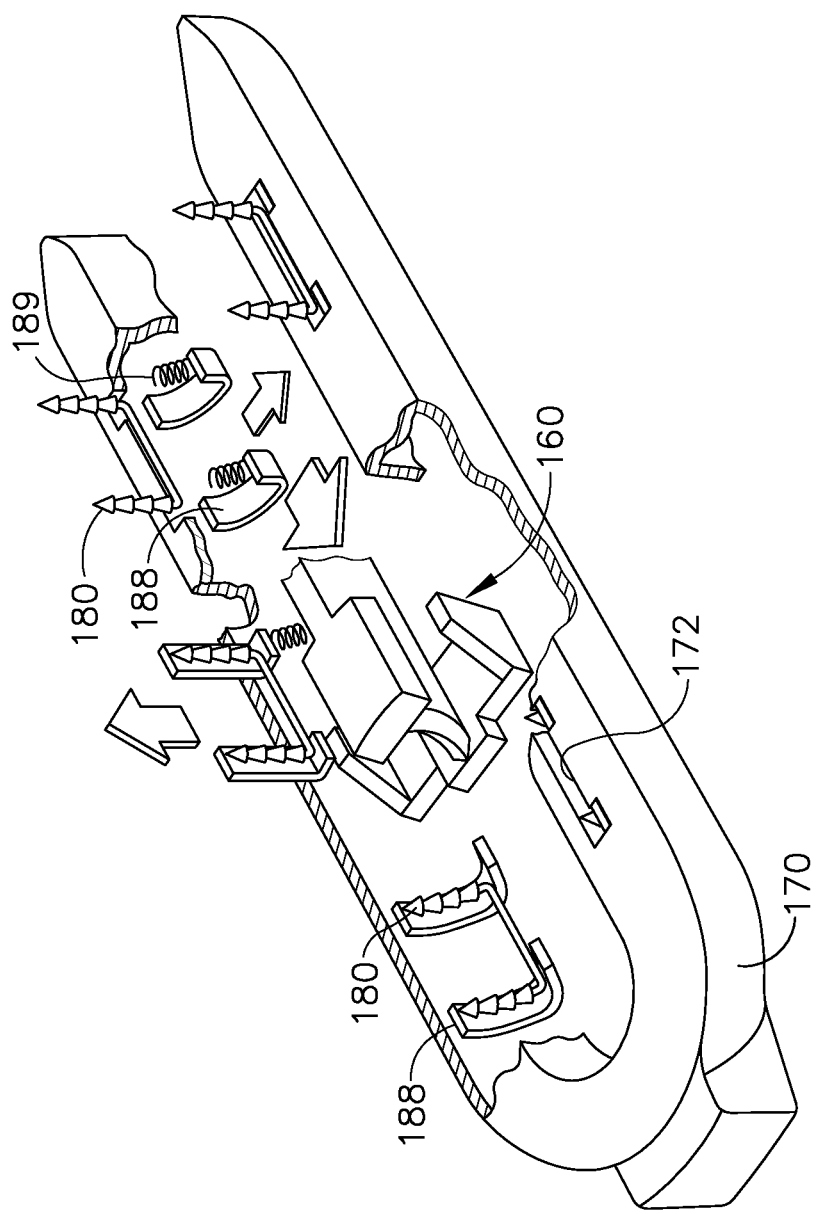

ELECTROSURGICAL END EFFECTOR WITH TISSUE TACKING FEATURES

BACKGROUND

A variety of surgical instruments include a tissue cutting element and one or more elements that transmit RF energy to tissue (e.g., to coagulate or seal the tissue). An example of such a device is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein; U.S. Pub. No. 2012/0116379, entitled "Motor Driven Electrosurgical Device with Mechanical and Electrical Feedback," published May 10, 2012, now U.S. Pat. No. 9,161,803, issued Oct. 20, 2015, the disclosure of which is incorporated by reference herein; U.S. Pub. No. 2012/0078243, entitled "Control Features for Articulating Surgical Device," published Mar. 29, 2012, the disclosure of which is incorporated by reference herein; U.S. Pub. No. 2012/0078247, entitled "Articulation Joint Features for Articulating Surgical Device," published Mar. 29, 2012, the disclosure of which is incorporated by reference herein; U.S. patent application Ser. No. 13/622,729, entitled "Surgical Instrument with Multi-Phase Trigger Bias," filed Sep. 19, 2012, now U.S. Pat. No. 9,089,327, issued Jul. 28, 2015, the disclosure of which is incorporated by reference herein; and U.S. patent application Ser. No. 13/622,735, entitled "Surgical Instrument with Contained Dual Helix Actuator Assembly," filed Sep. 19, 2012, now U.S. Pat. Pub. No. 2013/0023868, published Jan. 24, 2013, the disclosure of which is incorporated by reference herein.

While several medical devices have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 5A depicts a perspective view of another exemplary end effector for use with the instrument of FIG. 1, showing a separate tissue tacking cartridge;

FIG. 6A depicts a cross-sectional end view of the end effector and tissue tacking cartridge of FIG. 5A in a closed position, with the tissue tacking cartridge separated from the end effector;

FIG. 6B depicts a cross-sectional end view of the end effector and tissue tacking cartridge of FIG. 5A, coupled together;

FIG. 9 depicts a partial perspective view of the tissue tacking cartridge of FIG. 5A;

Figure 1:
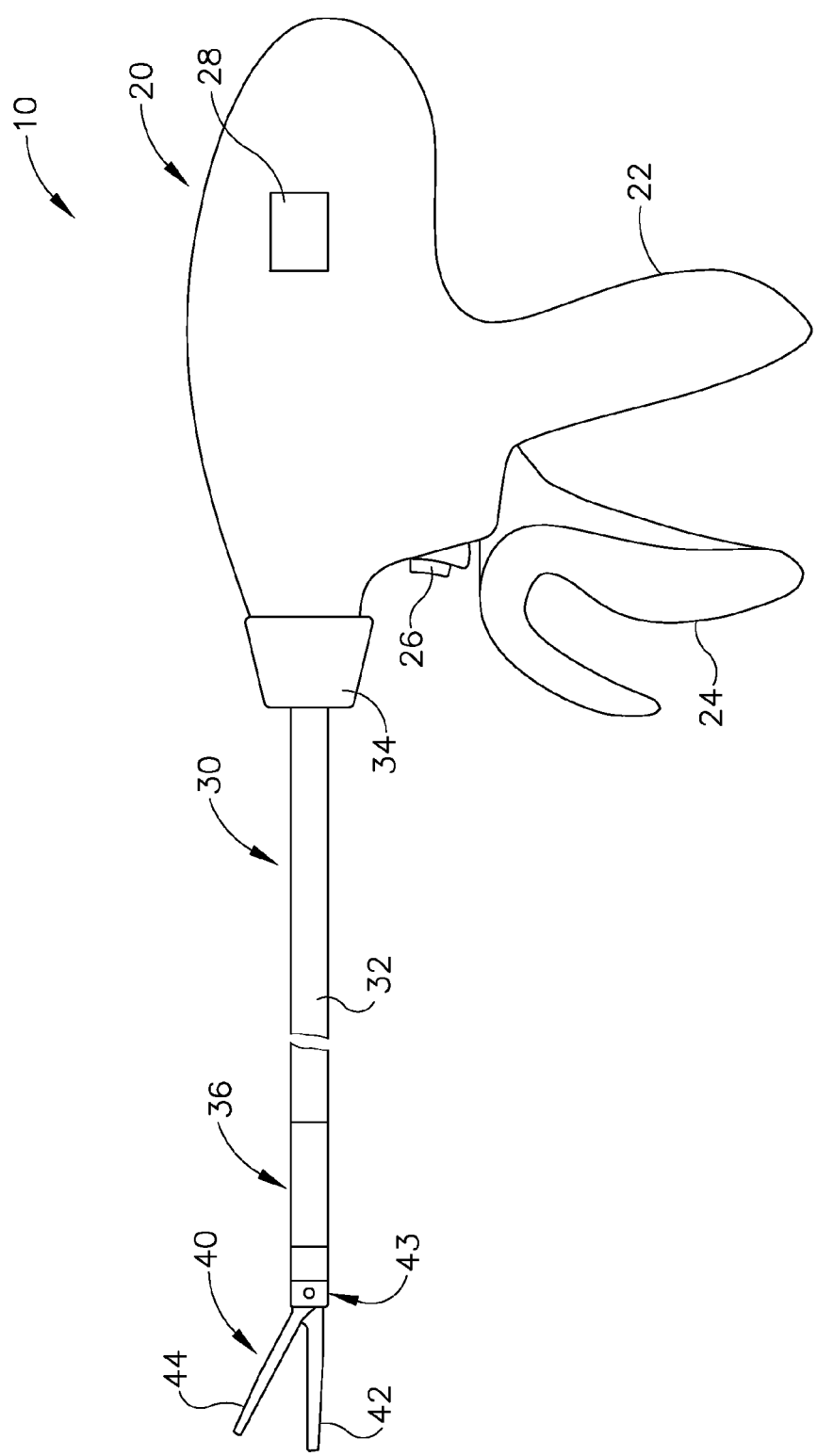
FIG. 1 depicts a side elevational view of an exemplary electrosurgical medical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Electrosurgical Device with Articulation Feature

FIGS. 1-4 show an exemplary electrosurgical instrument (10) that is constructed and operable in accordance with at least some of the teachings of U.S. Pat. No. 6,500,176; U.S. Pat. No. 7,112,201; U.S. Pat. No. 7,125,409; U.S. Pat. No. 7,169,146; U.S. Pat. No. 7,186,253; U.S. Pat. No. 7,189,233; U.S. Pat. No. 7,220,951; U.S. Pat. No. 7,309,849; U.S. Pat. No. 7,311,709; U.S. Pat. No. 7,354,440; U.S. Pat. No. 7,381,209; U.S. Pub. No. 2011/0087218, now U.S. Pat. No. 8,939,974; U.S. Pub. No. 2012/0116379, now U.S. Pat. No. 9,161,803; U.S. Pub. No. 2012/0078243; U.S. Pub. No. 2012/0078247; U.S. patent application Ser. No. 13/622,729; and/or U.S. patent application Ser. No. 13/622,735, now U.S. Pat. Pub. No. 2013/0023868. As described therein and as will be described in greater detail below, electrosurgical instrument (10) is operable to cut tissue and seal or weld tissue (e.g., a blood vessel, etc.) substantially simultaneously. In other words, electrosurgical instrument (10) operates similar to an endocutter type of stapler, except that electrosurgical instrument (10) provides tissue welding through application of bipolar RF energy instead of providing lines of staples to join tissue. It should also be understood that electrosurgical instrument (10) may have various structural and functional similarities with the ENSEAL® Tissue Sealing Device by Ethicon Endo-Surgery, Inc., of Cincinnati, Ohio. Furthermore, electrosurgical instrument (10) may have various structural and functional similarities with the devices taught in any of the other references that are cited and incorporated by reference herein. To the extent that there is some degree of overlap between the teachings of the references cited herein, the ENSEAL® Tissue Sealing Device by Ethicon Endo-Surgery, Inc., of Cincinnati, Ohio, and the following teachings relating to electrosurgical instrument (10), there is no intent for any of the description herein to be presumed as admitted prior art. Several teachings below will in fact go beyond the scope of the teachings of the references cited herein and the ENSEAL® Tissue Sealing Device by Ethicon Endo-Surgery, Inc., of Cincinnati, Ohio.

A. Exemplary Handpiece and Shaft

Electrosurgical instrument (10) of the present example includes a handpiece (20), a shaft (30) extending distally from handpiece (20), and an end effector (40) disposed at a distal end of shaft (30). Handpiece (20) of the present example includes a pistol grip (22), a pivoting trigger (24), an activation button (26), and an articulation control (28). Trigger (24) is pivotable toward and away from pistol grip (22) to selectively actuate end effector (40) as will be described in greater detail below. Activation button (26) is operable to selectively activate RF circuitry that is in communication with end effector (40), as will also be described in greater detail below. In some versions, activation button (26) also serves as a mechanical lockout against trigger (24), such that trigger (24) cannot be fully actuated unless button (26) is being pressed simultaneously. Examples of how such a lockout may be provided are disclosed in one or more of the references cited herein. In addition or in the alternative, trigger (24) may serve as an electrical and/or mechanical lockout against button (26), such that button (26) cannot be effectively activated unless trigger (24) is being squeezed simultaneously. It should be understood that pistol grip (22), trigger (24), and button (26) may be modified, substituted, supplemented, etc. in any suitable way, and that the descriptions of such components herein are merely illustrative.

Shaft (30) of the present example includes an outer sheath (32) and an articulation section (36). Articulation section (36) is operable to selectively position end effector (40) at various angles relative to the longitudinal axis defined by sheath (32). Articulation section (36) of shaft (30) may take a variety of forms. By way of example only, articulation section (36) may be configured in accordance with one or more teachings of U.S. Pub. No. 2012/0078247, the disclosure of which is incorporated by reference herein. As another merely illustrative example, articulation section (36) may be configured in accordance with one or more teachings of U.S. Pub. No. 2012/0078248, entitled "Articulation Joint Features for Articulating Surgical Device," published Mar. 29, 2012, now U.S. Pat. No. 9,220,559, issued Dec. 29, 2015, the disclosure of which is incorporated by reference herein. Various other suitable forms that articulation section (36) may take will be apparent to those of ordinary skill in the art in view of the teachings herein. It should also be understood that some versions of instrument (10) may simply lack articulation section (36).

In some versions, shaft (30) is also rotatable about the longitudinal axis defined by sheath (32), relative to handpiece (20), via a knob (34). Such rotation may provide rotation of end effector (40) and shaft (30) unitarily. In some other versions, knob (34) is operable to rotate end effector (40) without rotating any portion of shaft (30) that is proximal of articulation section (36). As another merely illustrative example, electrosurgical instrument (10) may include one rotation control that provides rotatability of shaft (30) and end effector (40) as a single unit; and another rotation control that provides rotatability of end effector (40) without rotating any portion of shaft (30) that is proximal of articulation section (36). Other suitable rotation schemes will be apparent to those of ordinary skill in the art in view of the teachings herein. Of course, rotatable features may simply be omitted if desired.

Articulation control (28) of the present example is operable to selectively control articulation section (36) of shaft (30), to thereby selectively position end effector (40) at various angles relative to the longitudinal axis defined by shaft (30). By way of example only, some merely illustrative forms that articulation control (28) and other components of handpiece (20) may take are disclosed in U.S. Pub. No. 2012/0078243, the disclosure of which is incorporated by reference herein; in U.S. Pub. No. 2012/0078244, entitled "Control Features for Articulating Surgical Device," published Mar. 29, 2012, the disclosure of which is incorporated by reference herein; and in U.S. patent application Ser. No. 13/622,735, now U.S. Pat. Pub. No. 2013/0023868, the disclosure of which is incorporated by reference herein. Still other suitable forms that articulation control (28) may take will be apparent to those of ordinary skill in the art in view of the teachings herein. It should also be understood that some versions of instrument (10) may simply lack an articulation control (28).

B. Exemplary End Effector

End effector (40) of the present example comprises a first jaw (42) and a second jaw (44). In the present example, second jaw (44) is substantially fixed relative to shaft (30); while first jaw (42) pivots relative to shaft (30), toward and away from second jaw (42). In some versions, actuators such as rods or cables, etc., may extend through sheath (32) and be joined with first jaw (42) at a pivotal coupling (43), such that longitudinal movement of the actuator rods/cables/etc. through shaft (30) provides pivoting of first jaw (42) relative to shaft (30) and relative to second jaw (44). Of course, jaws (42, 44) may instead have any other suitable kind of movement and may be actuated in any other suitable fashion. By way of example only, and as will be described in greater detail below, jaws (42, 44) may be actuated and thus closed by longitudinal translation of a firing beam (60), such that actuator rods/cables/etc. may simply be eliminated in some versions.

Figure 2:
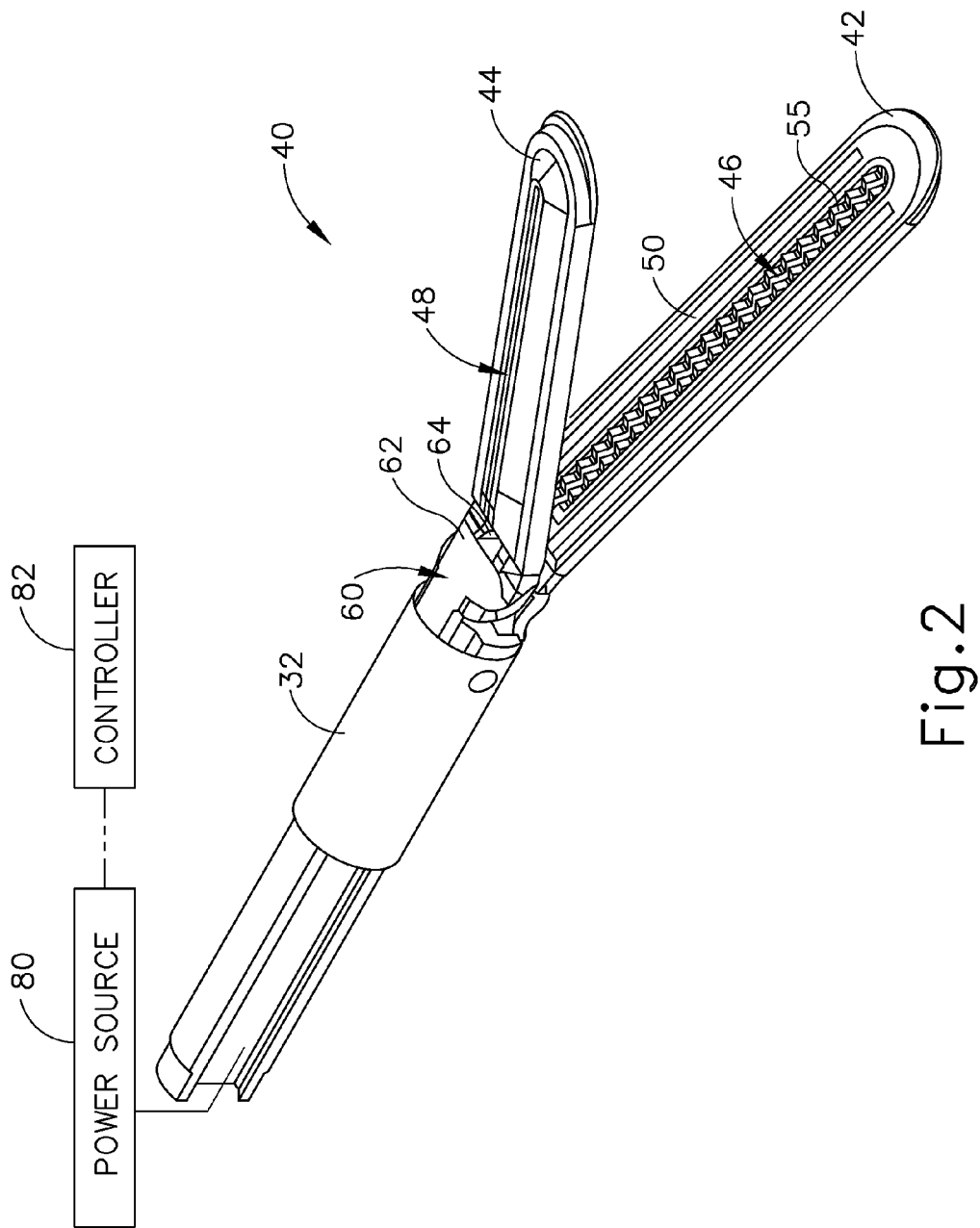
FIG. 2 depicts a perspective view of the end effector of the instrument of FIG. 1, in an open configuration.
Figure 3:
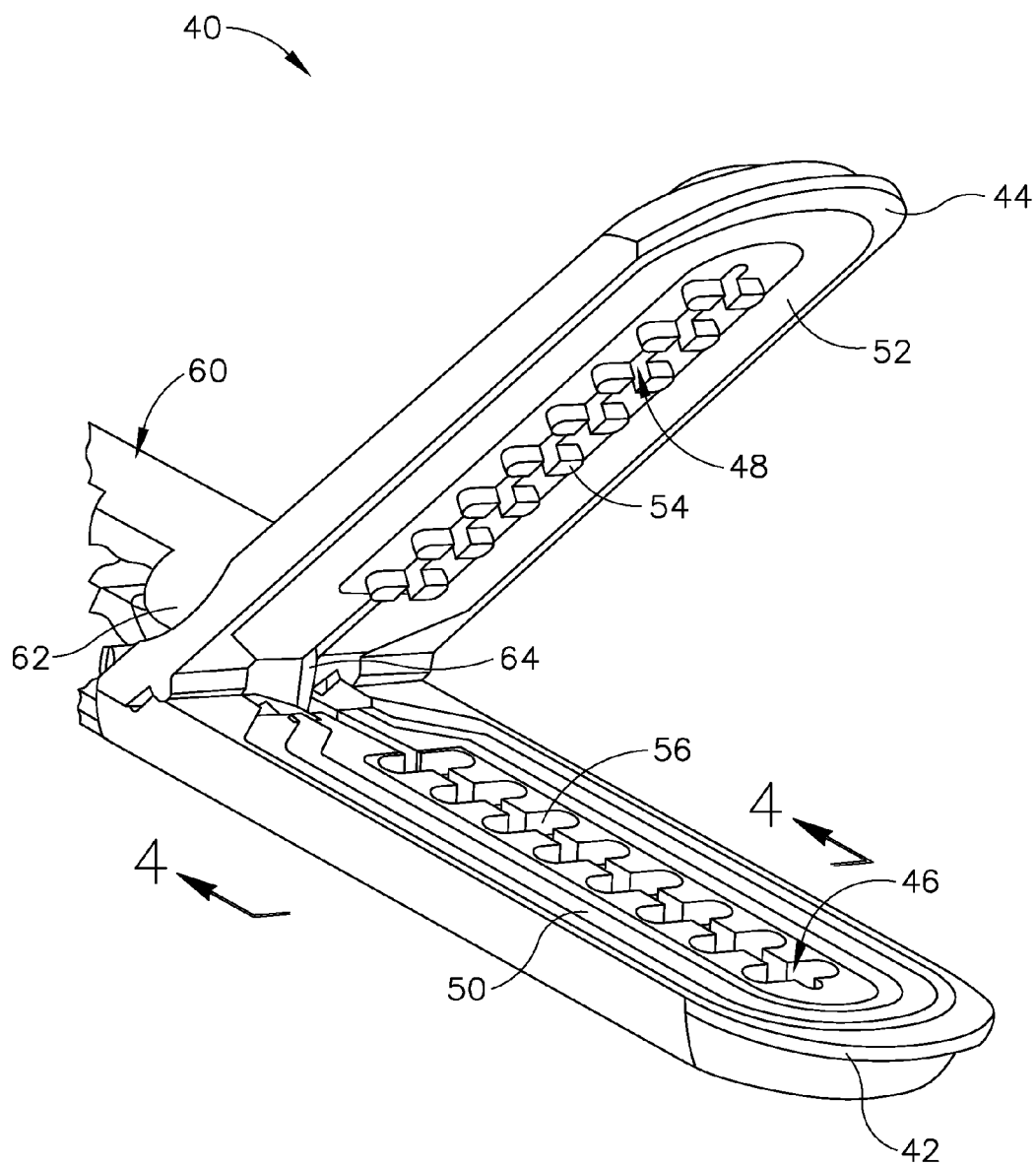
FIG. 3 depicts another perspective view of the end effector of the instrument of FIG. 1, in an open configuration.
Figure 4:
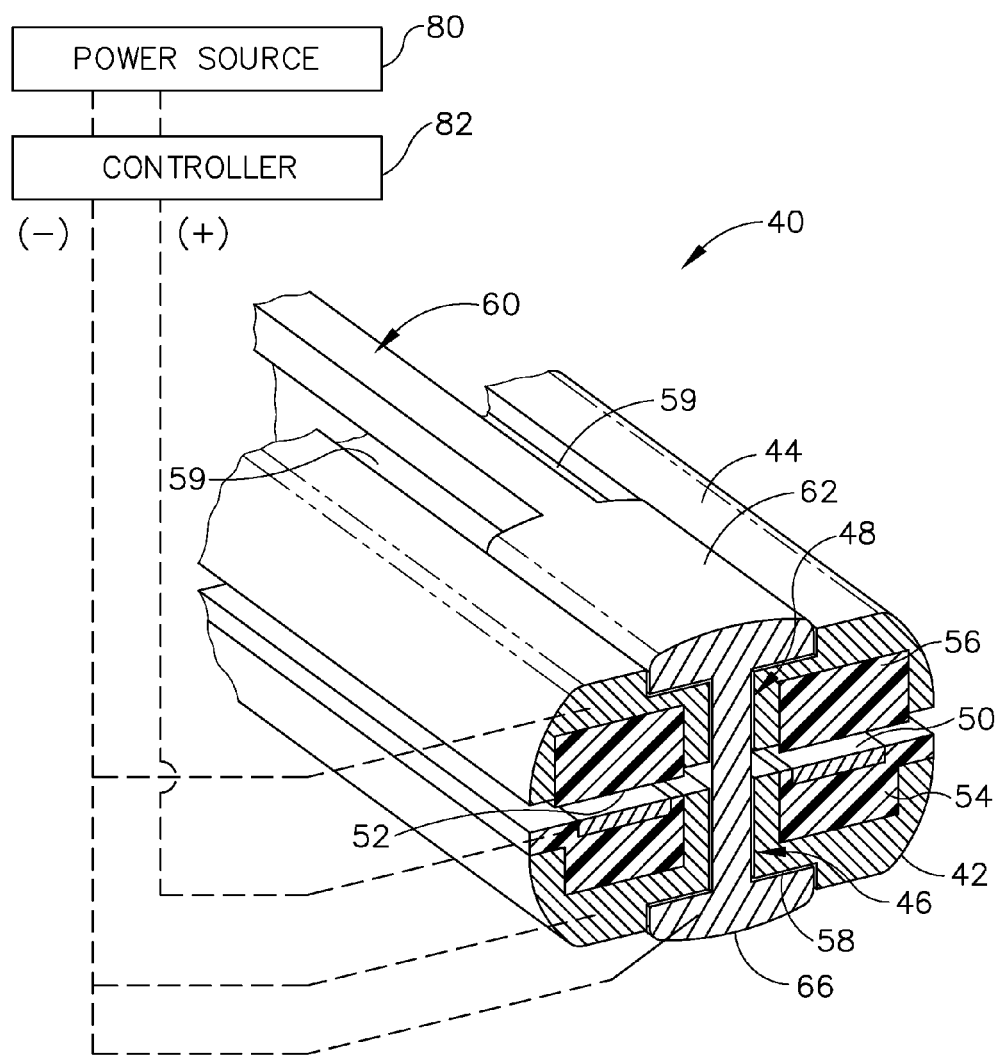
FIG. 4 depicts a cross-sectional end view of the end effector of FIG. 2, in a closed configuration and with the blade in a distal position, taken along line 4-4 of FIG. 3.

As best seen in FIGS. 2-4, first jaw (42) defines a longitudinally extending elongate slot (46); while second jaw (44) also defines a longitudinally extending elongate slot (48). In addition, the top side of first jaw (42) presents a first electrode surface (50); while the underside of second jaw (44) presents a second electrode surface (52). Electrode surfaces (50, 52) are in communication with an electrical source (80) via one or more conductors (not shown) that extend along the length of shaft (30). Electrical source (80) is operable to deliver RF energy to first electrode surface (50) at a first polarity and to second electrode surface (52) at a second (opposite) polarity, such that RF current flows between electrode surfaces (50, 52) and thereby through tissue captured between jaws (42, 44). In some versions, firing beam (60) serves as an electrical conductor that cooperates with electrode surfaces (50, 52) (e.g., as a ground return) for delivery of bipolar RF energy captured between jaws (42, 44). Electrical source (80) may be external to electrosurgical instrument (10) or may be integral with electrosurgical instrument (10) (e.g., in handpiece (20), etc.), as described in one or more references cited herein or otherwise. A controller (82) regulates delivery of power from electrical source (80) to electrode surfaces (50, 52). Controller (82) may also be external to electrosurgical instrument (10) or may be integral with electrosurgical instrument (10) (e.g., in handpiece (20), etc.), as described in one or more references cited herein or otherwise. It should also be understood that electrode surfaces (50, 52) may be provided in a variety of alternative locations, configurations, and relationships.

As best seen in FIG. 4, the lower side of first jaw (42) includes a longitudinally extending recess (59) adjacent to slot (46); while the upper side of second jaw (44) includes a longitudinally extending recess (58) adjacent to slot (48). FIG. 2 shows the upper side of first jaw (42) including a plurality of teeth serrations (46). It should be understood that the lower side of second jaw (44) may include complementary serrations that nest with serrations (46), to enhance gripping of tissue captured between jaws (42, 44) without necessarily tearing the tissue. FIG. 3 shows an example of serrations (46) in first jaw (42) as mainly recesses; with serrations (48) in second jaw (44) as mainly protrusions. Of course, serrations (46, 48) may take any other suitable form or may be simply omitted altogether. It should also be understood that serrations (46, 48) may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (42, 44).

With jaws (42, 44) in a closed position, shaft (30) and end effector (40) are sized and configured to fit through trocars having various inner diameters, such that electrosurgical instrument (10) is usable in minimally invasive surgery, though of course electrosurgical instrument (10) could also be used in open procedures if desired. By way of example only, with jaws (42, 44) in a closed position, shaft (30) and end effector (40) may present an outer diameter of approximately 5 mm. Alternatively, shaft (30) and end effector (40) may present any other suitable outer diameter (e.g., between approximately 2 mm and approximately 20 mm, etc.).

As another merely illustrative variation, either jaw (42, 44) or both of jaws (42, 44) may include at least one port, passageway, conduit, and/or other feature that is operable to draw steam, smoke, and/or other gases/vapors/etc. from the surgical site. Such a feature may be in communication with a source of suction, such as an external source or a source within handpiece (20), etc. In addition, end effector (40) may include one or more tissue cooling features (not shown) that reduce the degree or extent of thermal spread caused by end effector (40) on adjacent tissue when electrode surfaces (50, 52) are activated. Various suitable forms that such cooling features may take will be apparent to those of ordinary skill in the art in view of the teachings herein.

In some versions, end effector (40) includes one or more sensors (not shown) that are configured to sense a variety of parameters at end effector (40), including but not limited to temperature of adjacent tissue, electrical resistance or impedance of adjacent tissue, voltage across adjacent tissue, forces exerted on jaws (42, 44) by adjacent tissue, etc. By way of example only, end effector (40) may include one or more positive temperature coefficient (PTC) thermistor bodies (54, 56) (e.g., PTC polymer, etc.), located adjacent to electrodes (50, 52) and/or elsewhere. Data from sensors may be communicated to controller (82). Controller (82) may process such data in a variety of ways. By way of example only, controller (82) may modulate or otherwise change the RF energy being delivered to electrode surfaces (50, 52), based at least in part on data acquired from one or more sensors at end effector (40). In addition or in the alternative, controller (82) may alert the user to one or more conditions via an audio and/or visual feedback device (e.g., speaker, lights, display screen, etc.), based at least in part on data acquired from one or more sensors at end effector (40). It should also be understood that some kinds of sensors need not necessarily be in communication with controller (82), and may simply provide a purely localized effect at end effector (40). For instance, a PTC thermistor bodies (54, 56) at end effector (40) may automatically reduce the energy delivery at electrode surfaces (50, 52) as the temperature of the tissue and/or end effector (40) increases, thereby reducing the likelihood of overheating. In some such versions, a PTC thermistor element is in series with power source (80) and electrode surface (50, 52); and the PTC thermistor provides an increased impedance (reducing flow of current) in response to temperatures exceeding a threshold. Furthermore, it should be understood that electrode surfaces (50, 52) may be used as sensors (e.g., to sense tissue impedance, etc.). Various kinds of sensors that may be incorporated into electrosurgical instrument (10) will be apparent to those of ordinary skill in the art in view of the teachings herein. Similarly various things that can be done with data from sensors, by controller (82) or otherwise, will be apparent to those of ordinary skill in the art in view of the teachings herein. Other suitable variations for end effector (40) will also be apparent to those of ordinary skill in the art in view of the teachings herein.

C. Exemplary Firing Beam

As also seen in FIGS. 2-4, electrosurgical instrument (10) of the present example includes a firing beam (60) that is longitudinally movable along part of the length of end effector (40). Firing beam (60) is coaxially positioned within shaft (30), extends along the length of shaft (30), and translates longitudinally within shaft (30) (including articulation section (36) in the present example), though it should be understood that firing beam (60) and shaft (30) may have any other suitable relationship. Firing beam (60) includes a sharp distal blade (64), an upper flange (62), and a lower flange (66). As best seen in FIG. 4, distal blade (64) extends through slots (46, 48) of jaws (42, 44), with upper flange (62) being located above jaw (44) in recess (59) and lower flange (66) being located below jaw (42) in recess (58). The configuration of distal blade (64) and flanges (62, 66) provides an "I-beam" type of cross section at the distal end of firing beam (60). While flanges (62, 66) extend longitudinally only along a small portion of the length of firing beam (60) in the present example, it should be understood that flanges (62, 66) may extend longitudinally along any suitable length of firing beam (60). In addition, while flanges (62, 66) are positioned along the exterior of jaws (42, 44), flanges (62, 66) may alternatively be disposed in corresponding slots formed within jaws (42, 44). For instance, each jaw (42, 44) may define a "T"-shaped slot, with parts of distal blade (64) being disposed in one vertical portion of each "T"-shaped slot and with flanges (62, 66) being disposed in the horizontal portions of the "T"-shaped slots. Various other suitable configurations and relationships will be apparent to those of ordinary skill in the art in view of the teachings herein.

Distal blade (64) is substantially sharp, such that distal blade (64) will readily sever tissue that is captured between jaws (42, 44). Distal blade (64) is also electrically grounded in the present example, providing a return path for RF energy as described elsewhere herein. In some other versions, distal blade (64) serves as an active electrode. In addition or in the alternative, distal blade (64) may be selectively energized with ultrasonic energy (e.g., harmonic vibrations at approximately 55.5 kHz, etc.).

The "I-beam" type of configuration of firing beam (60) provides closure of jaws (42, 44) as firing beam (60) is advanced distally. In particular, flange (62) urges jaw (44) pivotally toward jaw (42) as firing beam (60) is advanced from a proximal position (FIGS. 1-3) to a distal position (FIG. 4), by bearing against recess (59) formed in jaw (44). This closing effect on jaws (42, 44) by firing beam (60) may occur before distal blade (64) reaches tissue captured between jaws (42, 44). Such staging of encounters by firing beam (60) may reduce the force required to squeeze grip (24) to actuate firing beam (60) through a full firing stroke. In other words, in some such versions, firing beam (60) may have already overcome an initial resistance required to substantially close jaws (42, 44) on tissue before encountering resistance from severing the tissue captured between jaws (42, 44). Of course, any other suitable staging may be provided.

In the present example, flange (62) is configured to cam against a ramp feature at the proximal end of jaw (44) to open jaw (42) when firing beam (60) is retracted to a proximal position and to hold jaw (42) open when firing beam (60) remains at the proximal position. This camming capability may facilitate use of end effector (40) to separate layers of tissue, to perform blunt dissections, etc., by forcing jaws (42, 44) apart from a closed position. In some other versions, jaws (42, 44) are resiliently biased to an open position by a spring or other type of resilient feature. While jaws (42, 44) close or open as firing beam (60) is translated in the present example, it should be understood that other versions may provide independent movement of jaws (42, 44) and firing beam (60). By way of example only, one or more cables, rods, beams, or other features may extend through shaft (30) to selectively actuate jaws (42, 44) independently of firing beam (60). Such jaw (42, 44) actuation features may be separately controlled by a dedicated feature of handpiece (20). Alternatively, such jaw actuation features may be controlled by trigger (24) in addition to having trigger (24) control firing beam (60). It should also be understood that firing beam (60) may be resiliently biased to a proximal position, such that firing beam (60) retracts proximally when a user relaxes their grip on trigger (24).

D. Exemplary Operation

In an exemplary use, end effector (40) is inserted into a patient via a trocar. Articulation section (36) is substantially straight when end effector (40) and part of shaft (30) are inserted through the trocar. Articulation control (28) may then be manipulated to pivot or flex articulation section (36) of shaft (30) in order to position end effector (40) at a desired position and orientation relative to an anatomical structure within the patient. Two layers of tissue of the anatomical structure are then captured between jaws (42, 44) by squeezing trigger (24) toward pistol grip (22). Such layers of tissue may be part of the same natural lumen defining anatomical structure (e.g., blood vessel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of electrosurgical instrument (10) is perpendicular to the longitudinal axis defined by end effector (40), etc.). In other words, the lengths of jaws (42, 44) may be oriented perpendicular to (or at least generally transverse to) the length of the blood vessel. As noted above, flanges (62, 66) cammingly act to pivot jaw (42) toward jaw (44) when firing beam (60) is actuated distally by squeezing trigger (24) toward pistol grip (22). Jaws (42, 44) may be substantially clamping tissue before trigger (24) has swept through a full range of motion toward pistol grip (22), such that trigger (24) may continue pivoting toward pistol grip (22) through a subsequent range of motion after jaws (42, 44) have substantially clamped on the tissue.

With tissue layers captured between jaws (42, 44) firing beam (60) continues to advance distally by the user squeezing trigger (24) further toward pistol grip (22). As firing beam (60) continues to advance distally, distal blade (64) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of flanges (62, 66) immediately above and below jaws (42, 44), respectively, may help keep jaws (42, 44) in a closed and tightly clamping position. In particular, flanges (62, 66) may help maintain a significantly compressive force between jaws (42, 44). With severed tissue layer portions being compressed between jaws (42, 44), electrode surfaces (50, 52) are activated with bipolar RF energy by the user depressing activation button (26). In some versions, electrodes (50, 52) are selectively coupled with power source (80) (e.g., by the user depressing button (26), etc.) such that electrode surfaces (50, 52) of jaws (42, 44) are activated with a common first polarity while firing beam (60) is activated at a second polarity that is opposite to the first polarity. Thus, a bipolar RF current flows between firing beam (60) and electrode surfaces (50, 52) of jaws (42, 44), through the compressed regions of severed tissue layer portions. In some other versions, electrode surface (50) has one polarity while electrode surface (52) and firing beam (60) both have the other polarity. In either version (among at least some others), bipolar RF energy delivered by power source (80) ultimately thermally welds the tissue layer portions on one side of firing beam (60) together and the tissue layer portions on the other side of firing beam (60) together.

In certain circumstances, the heat generated by activated electrode surfaces (50, 52) can denature the collagen within the tissue layer portions and, in cooperation with clamping pressure provided by jaws (42, 44), the denatured collagen can form a seal within the tissue layer portions. Thus, the severed ends of the natural lumen defining anatomical structure are hemostatically sealed shut, such that the severed ends will not leak bodily fluids. In some versions, electrode surfaces (50, 52) may be activated with bipolar RF energy before firing beam (60) even begins to translate distally and thus before the tissue is even severed. For instance, such timing may be provided in versions where button (26) serves as a mechanical lockout relative to trigger (24) in addition to serving as a switch between power source (80) and electrode surfaces (50, 52). Other suitable ways in which instrument (10) may be operable and operated will be apparent to those of ordinary skill in the art in view of the teachings herein.

II. Exemplary Tissue Tacking Features

In some instances, it may be desirable to reinforce the seal created by the RF energy delivered by end effector (40). For example, reinforcement may be desired when a patient experiences an unforeseen trauma before healing of the tissue is complete, or during procedures, such as a lung parenchyma, where the lungs may have a lower amount of collagen in the tissue and experience a high volume increase due to breathing and coughing. Such reinforcement may be provided to the lungs, or any other desired tissue, by deploying mechanical fasteners from end effector (40) to tack the apposed tissue layer portions. The mechanical fasteners may be housed within end effector (40) outside of electrode surfaces (50, 52) so as to not impact the fluid tight seal created by electrode surfaces (50, 52). This may provide a more isolated or continuous support between the apposed tissue layer portions. Because jaws (42, 44) of end effector (40) may not have a sufficient amount of room to house the fasteners in some instances, the mechanical fasteners may also be provided in tissue tacking cartridges that couple with end effector (40). The examples below include several merely illustrative versions of mechanical fasteners that may be readily introduced to an end effector (40).

A. Exemplary Tissue Tacking Cartridges

Fasteners may be provided in a disposable or replaceable tissue tacking cartridge that couples to end effector (40). For example, a tissue tacking cartridge may engage lower or fixed jaw (42) to align mechanical fasteners around the outside of electrode surface (50). By coupling the cartridge to lower jaw (42), only the footprint of lower jaw (42) is increased, allowing upper jaw (44) to move and continue to be positioned around small spaces. Alternatively, a cartridge may be coupled to upper jaw (44). A cartridge also allows a surgeon to choose to attach a cartridge only when he or she desires to fire fasteners, without interfering with the RF activities described above to seal the tissue layer portions. A surgeon may reload or replace the cartridge after firing to provide additional fasteners. The examples below provide several versions of disposable or replaceable tissue tacking cartridges that may be readily coupled to end effector (40). In some versions, a puncturable film or other cover is provided to retain tacks in a cartridge, without unduly interfering with their deployment, to prevent the tacks from falling out inadvertently.

1. Exemplary Snap-On Tissue Tacking Cartridge

Figure 5B:
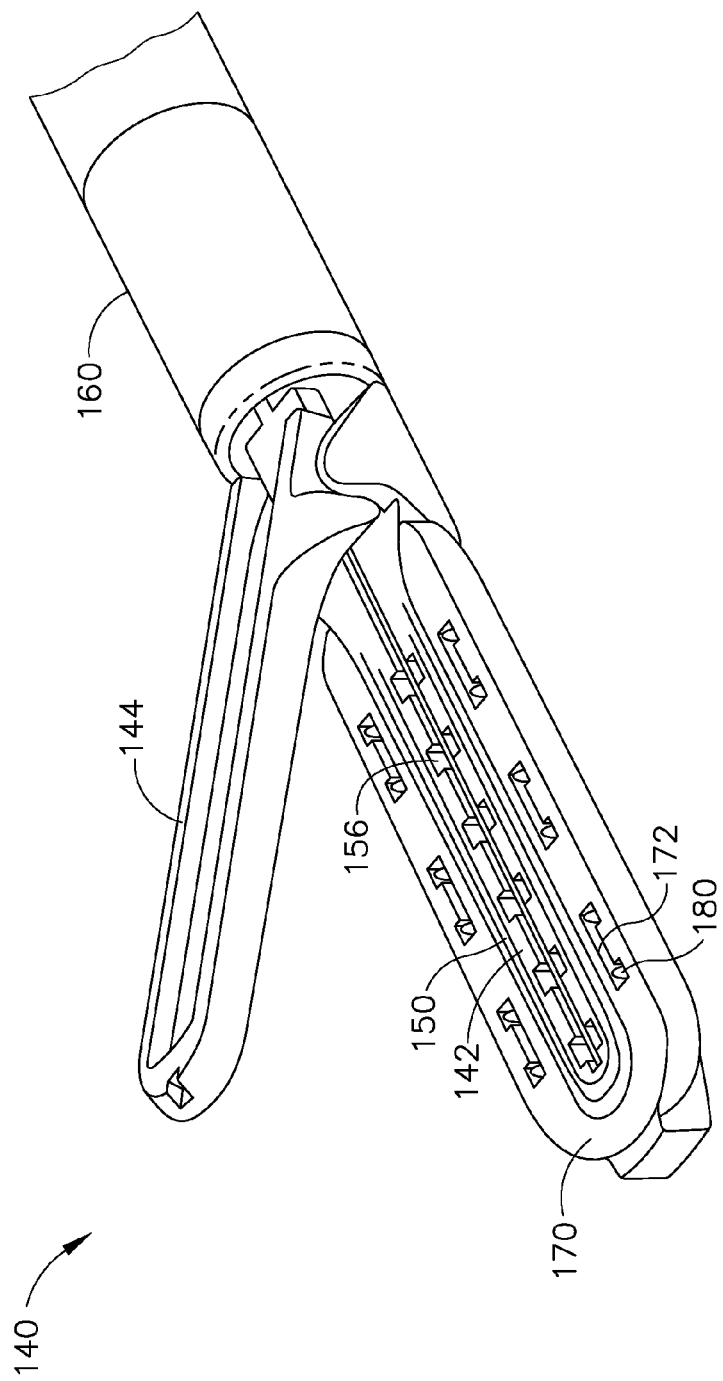
FIG. 5B depicts a perspective view of the end effector of FIG. 5A, showing the tissue tacking cartridge coupled to the end effector.

FIGS. 5A-12 show an exemplary snap-on tissue tacking cartridge (170) for coupling with end effector (140). End effector (140) is similar to end effector (40), except that the lower jaw (142) of end effector (140) comprises engagement recesses (158). Engagement recesses (158) are aligned around the outer wall of lower jaw (142), as shown in FIG. 5A. Engagement recesses (158) may also be provided on a bottom surface of lower jaw (142). Tissue tacking cartridge (170) comprises a bottom wall (176), a side wall (178) extending from bottom wall (176) such that side wall (178) comprises a top surface (179). Bottom wall (176) is sized to correspond to the bottom surface of lower jaw (142). Side wall (178) is configured to extend from bottom wall (176) to correspond to the side wall of lower jaw (142) such that top surface (179) is flush with the top surface of lower jaw (142) when cartridge (170) is coupled to lower jaw (142), as shown in FIG. 5B.

As shown in FIG. 5A, side wall (178) of cartridge (170) comprises protrusions (174) aligned to correspond to engagement recesses (158) of lower jaw (142). When cartridge (170) is coupled to lower jaw (142), protrusions (174) fit within engagement recesses (158) to secure cartridge (170) to lower jaw (142) and ensure proper positioning of cartridge (170) on lower jaw (142). As cartridge (170) is coupled to lower jaw (142), side wall (178) may flex outward until protrusions (174) are aligned with engagement recesses (158). To insert protrusions (174) within engagement recesses (158), side wall (178) may flex back inwardly to the original position, such that cartridge (170) is secured to lower jaw (142) through a snap fit, as shown in FIG. 5B. Side wall (178) of cartridge (170) further comprises a plurality of fastener recesses (172) extending from top surface (179). Each fastener recess (172) may store a fastener (180). As shown in FIGS. 6A-6B, fastener recess (172) has a depth that is greater than the height of fastener (180), such that fastener (180) does not protrude from fastener recess (172). This may prevent a fastener (180) from inadvertently engaging tissue before fasteners (180) are deployed.

Figure 7:
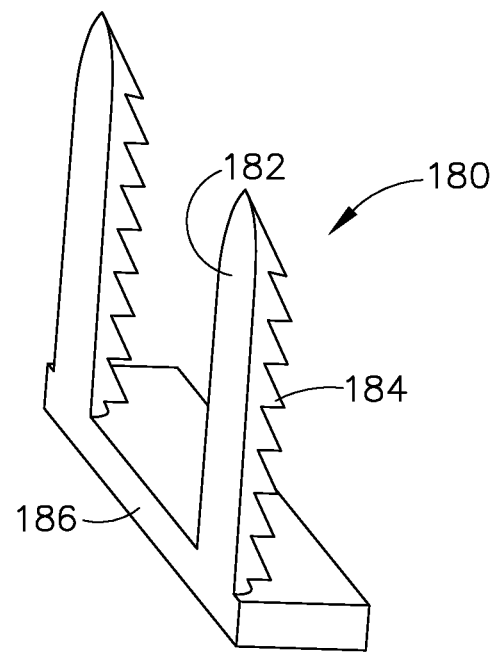
FIG. 7 depicts a perspective view of a fastener of the tissue tacking cartridge of FIG. 5A.

An exemplary fastener (180) is shown in FIG. 7. Fastener (180) comprises a base (186), protrusions (182) extending from base (186), and barbs (184) positioned along protrusions (182). The top of protrusions (182) are pointed to more easily penetrate tissue. When fastener (180) is deployed from cartridge (170), protrusions (182) may penetrate tissue until base (186) contacts a bottom surface of the tissue to stop fastener (180) from advancing further. Base (186) may also provide reinforcement support along the entire length of fastener (180). Barbs (184) are comprise angled surfaces, which may puncture tissue in one direction, but prevent fastener (180) from being pulled back out in the direction fastener (180) was inserted. Instead of barbs (184), fastener (180) may also comprise a t-tag at the top of protrusions (182) to prevent fastener (180) from being pulled back out from tissue. Other suitable fastener (180) configurations will be apparent to one with ordinary skill in the art in view of the teachings herein.

Fasteners (180) may be made of a non-conductive material to prevent interference with electrode surfaces (150, 152). Fasteners (180) may also be absorbable such that fasteners (180) are absorbed by the body after the tissue has had a sufficient amount of time to heal. Alternatively, fasteners (180) may be manually removed. The configuration of fastener (180) allows fastener (180) to be retained within tissue without the need for a staple forming pocket or for any other anvil feature to drive fastener (180) against. However, other fastener (180) configurations may be used that may require an anvil comprising staple forming pockets or other features on adjacent jaw (144).

Figure 8:
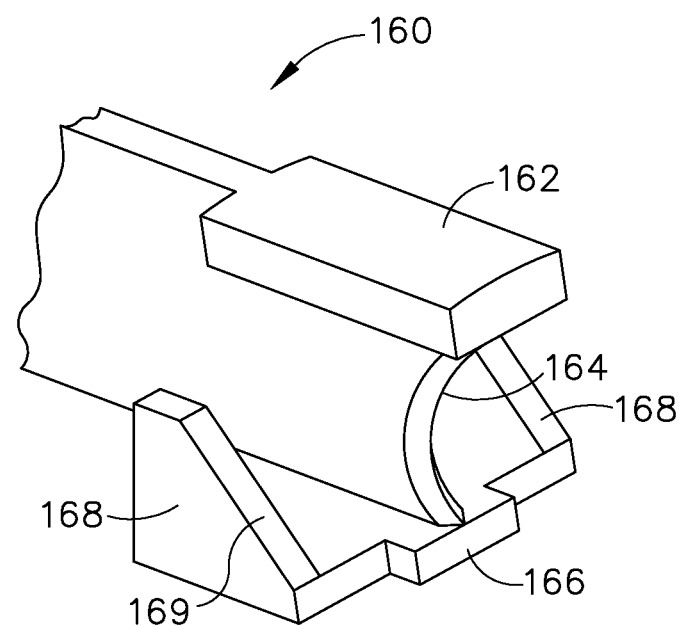
FIG. 8 depicts a perspective view of the distal end of a firing beam of the end effector of FIG. 5A.

Fasteners (180) may be deployed from cartridge (170) by firing beam (160). Firing beam (160) of this example is similar to firing beam (60), except that firing beam (160) comprises fastener driving cams (168). As shown in FIG. 8, firing beam (160) comprises a blade (164) extending between upper flange (162) and lower flange (166). Lower flange (166) extends beyond upper flange (162). Fastener driving cams (168) extend from lower flange (166) to top surface (179) of cartridge (179). This allows fastener driving cams (168) to fully deploy fasteners (180) from fastener recesses (172). The front of fastener driving cams (168) comprise angled surfaces (169) to aid in deploying fasteners (180). As firing beam (160) advances through lower jaw (142), angled surfaces (169) on fastener driving cams (168) contact fasteners (180) and push them up and out of fastener recesses (172). Alternatively, fastener driving cams (168) may be provided on a separate sled contained within cartridge (170). Firing beam (160) may then be configured similar to firing beam (60) and could simply push the sled to deploy fasteners (180). Fastener driving cams (168) may either directly contact fasteners (180), or may drive fasteners (180) via spring-loaded drivers (188) located in fastener recess (172).

Figure 10A:
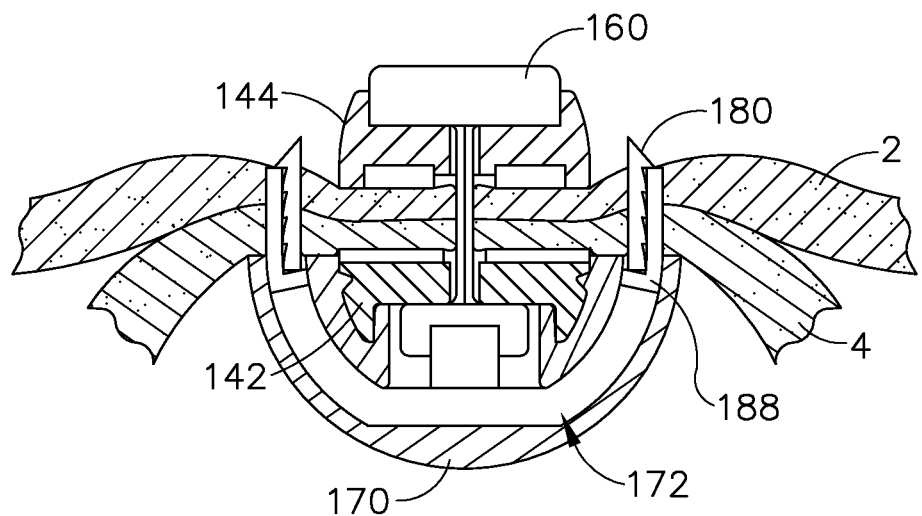
FIG. 10A depicts a cross-sectional view of the end effector of FIG. 5A showing the firing beam cutting through tissue and driving tacks into tissue.
Figure 10B:
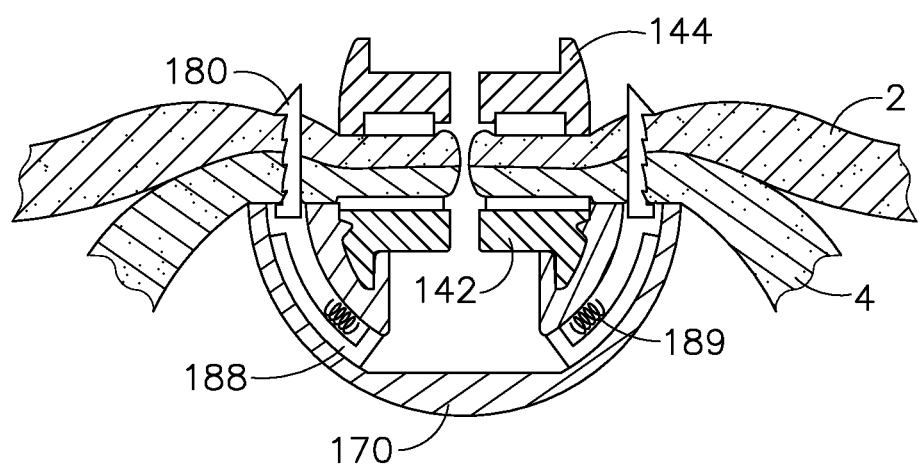
FIG. 10B depicts a cross-sectional view of the end effector of FIG. 5A showing tissue that has been cut and tacked, with the firing beam retracted.
Figure 11A:
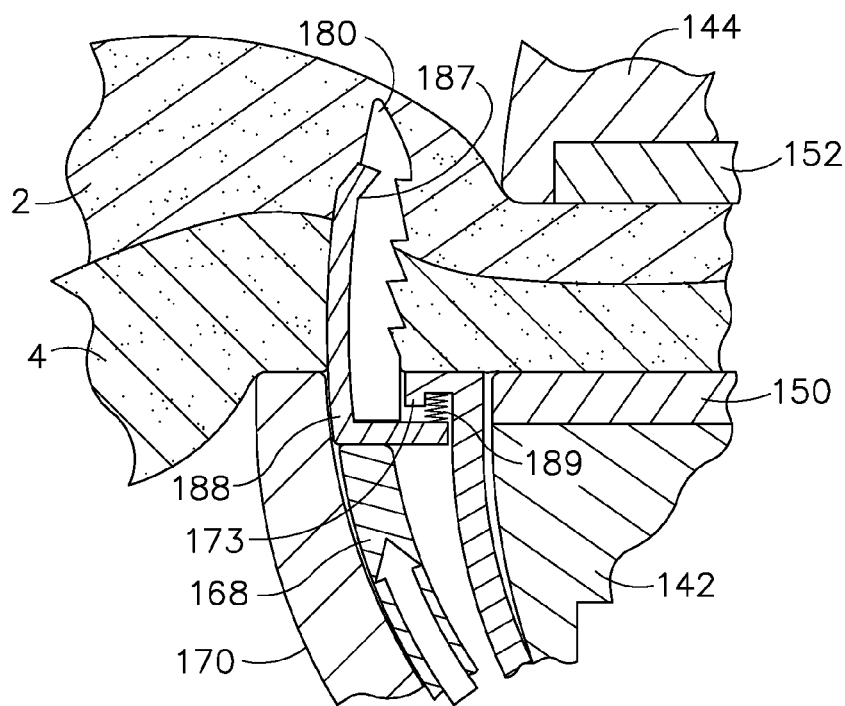
FIG. 11A depicts a partial cross-sectional view of the tissue tacking cartridge of FIG. 5A applying a fastener through tissue.
Figure 11B:
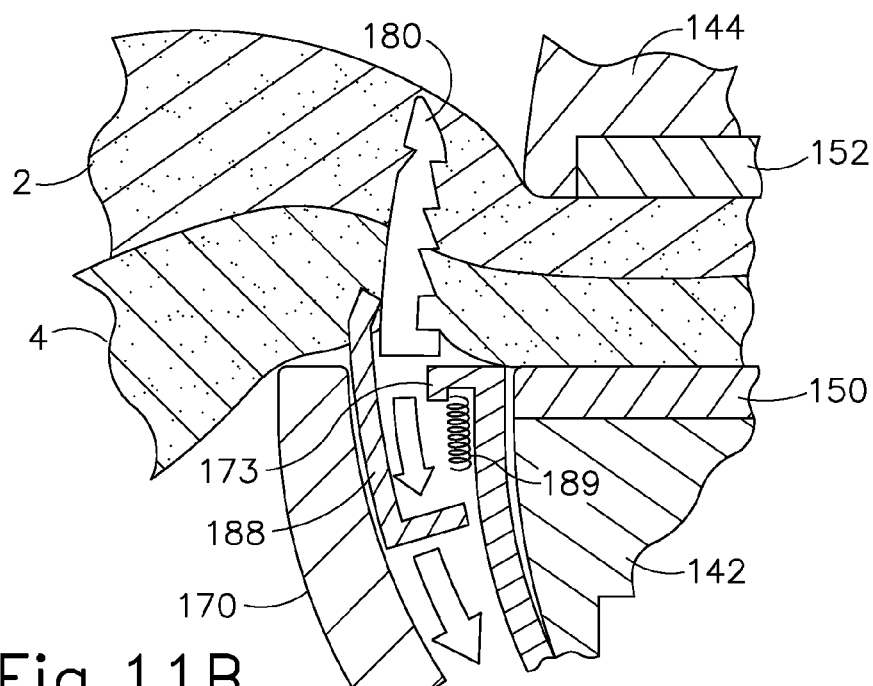
FIG. 11B depicts a partial cross-sectional view of the tissue tacking cartridge of FIG. 5A, showing the fastener applied to tissue.

As shown in FIGS. 9-11B, a driver (188) is configured to guide fastener (180). A separate driver (188) is provided for each protrusion (182) of fastener (180) in this example, though other driver (188) configurations may be provided. Driver (188) comprises a wall and a base extending outwardly from the wall. Protrusions (182) of fastener (180) rest against the wall of driver (188), while base (186) of fastener (180) rests against the base of driver (188). The wall of driver (188) angles inwardly at the top and is received in a notch of protrusion (182) to provide support for fastener (180) as fastener (180) is deployed through tissue without obstructing the tip of fastener (180), as shown in FIG. 11A. A resilient member (189) is placed between driver (188) and the top surface of fastener recess (172). Resilient member (189) biases driver (188) into fastener recess (172). Resilient member (189) compresses as receptacle (188) is pushed upward by firing beam (160) and biases driver (188) back into fastener recess (172) after firing beam (160) has passed and fastener (180) has been deployed, as shown in FIG. 11B. The top surface of fastener recess (172) comprises a hook (173) to retain resilient member (189) within fastener recess (172).

In operation, tissue tacking cartridge (170) may be coupled to lower jaw (142) by sliding cartridge (170) upward onto lower jaw (142), as shown in FIGS. 5A-5B. As cartridge (170) slides upward along lower jaw (142), side wall (178) of cartridge (170) may flex outward. When protrusions (174) along side wall (178) align with engagement recesses (158) of lower jaw (142), side wall (178) flexes inward to insert protrusions (174) within engagement recesses (158). The fit between protrusions (174) and engagement recesses (158) secure cartridge (170) to lower jaw (142). End effector (140) may then be inserted into a patient via a trocar. Articulation control (28) may then be manipulated to pivot or flex articulation section (36) of shaft (30) in order to position end effector (140) at a desired position and orientation relative to an anatomical structure within the patient. Two layers of tissue of the anatomical structure are then captured between jaws (142, 144) by squeezing trigger (24) toward pistol grip (22). Flanges (162, 166) cammingly act to pivot jaw (142) toward jaw (144) when firing beam (160) is actuated distally by squeezing trigger (24) toward pistol grip (22). Jaws (142, 144) may be substantially clamping tissue before trigger (24) has swept through a full range of motion toward pistol grip (22), such that trigger (24) may continue pivoting toward pistol grip (22) through a subsequent range of motion after jaws (142, 144) have substantially clamped on the tissue.

With tissue layers captured between jaws (142, 144) firing beam (160) continues to advance distally by the user squeezing trigger (24) further toward pistol grip (22). As firing beam (160) continues to advance distally, distal blade (164) simultaneously severs the clamped tissue layers, resulting in separated upper layer portions being apposed with respective separated lower layer portions. With severed tissue layer portions being compressed between jaws (142, 144), electrode surfaces (150, 152) are activated with bipolar RF energy by the user depressing activation button (26). In some versions, electrodes (150, 152) are selectively coupled with power source (80) (e.g., by the user depressing button (26), etc.) such that electrode surfaces (150, 152) of jaws (142, 144) are activated with a common first polarity while firing beam (160) is activated at a second polarity that is opposite to the first polarity. Thus, a bipolar RF current flows between firing beam (160) and electrode surfaces (150, 152) of jaws (142, 144), through the compressed regions of severed tissue layer portions. In some other versions, electrode surface (150) has one polarity while electrode surface (152) and firing beam (160) both have the other polarity. In either version (among at least some others), bipolar RF energy delivered by power source (80) ultimately thermally welds the tissue layer portions on one side of firing beam (160) together and the tissue layer portions on the other side of firing beam (160) together.

Figure 12:
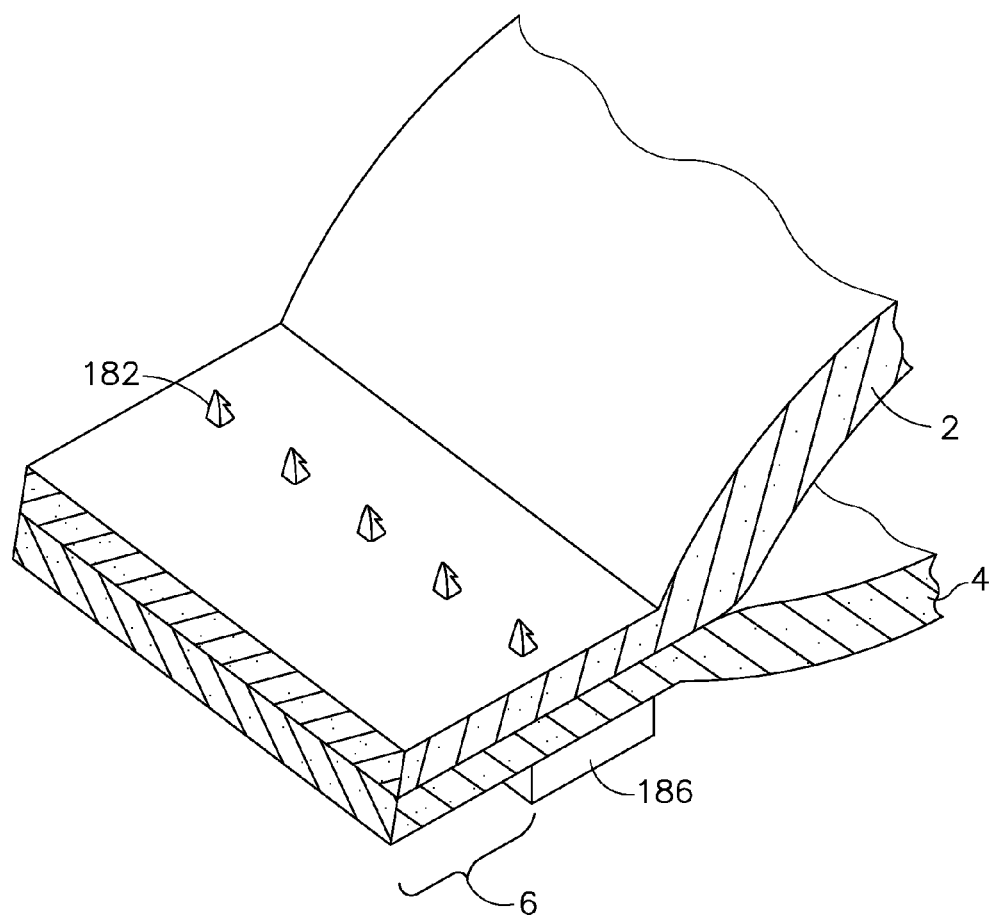
FIG. 12 depicts a perspective view of the tissue of FIG. 11B that has been severed and tacked.
Figure 13:
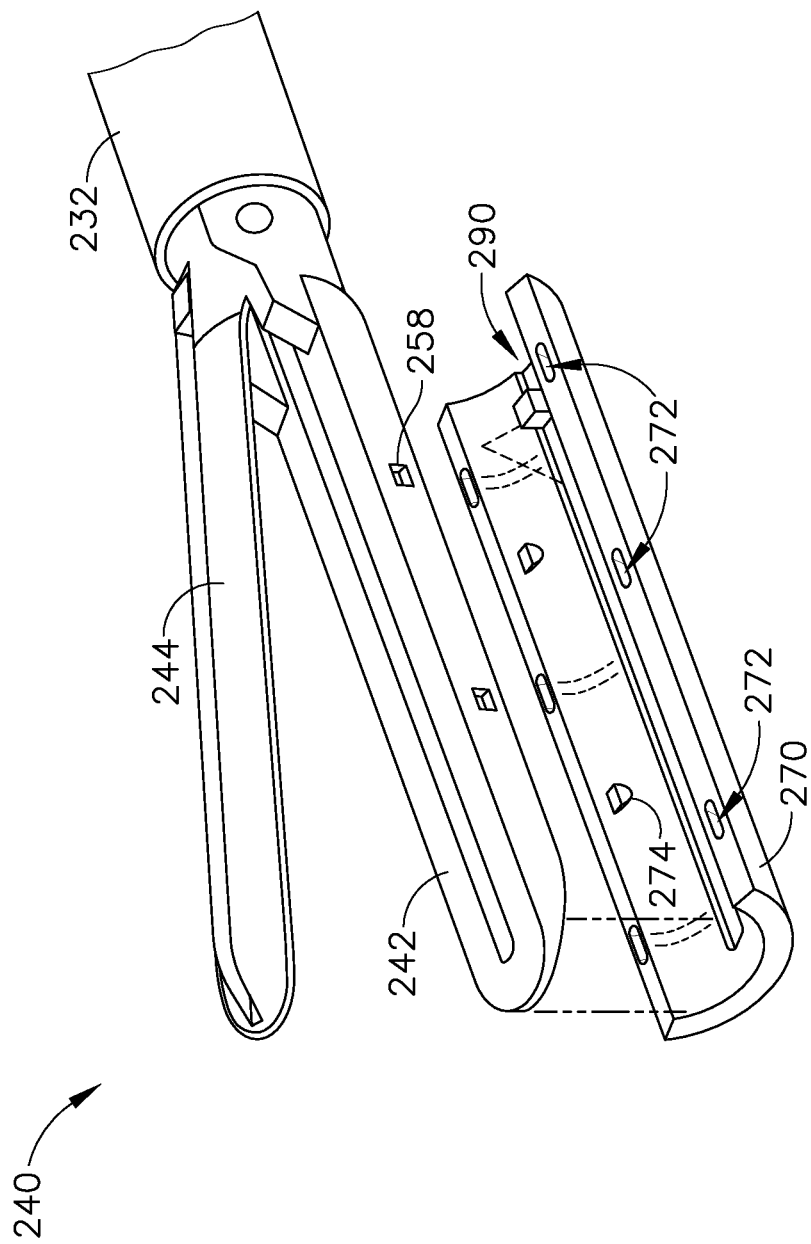
FIG. 13 depicts a perspective view of another exemplary end effector for use with the instrument of FIG. 1, showing a tissue tacking cartridge.

As firing beam (160) advances, angled surfaces (169) on fastener driving cams (168) contact drivers (188) to push drivers (188) up through fastener recesses (172), as shown in FIGS. 9, 10A, and 11A. When drivers (188) move upward, fasteners (180) penetrate the tissue layer portions outside of the thermal weld zone of electrode surfaces (150, 152). Drivers (188) may include sharp tips to assist with tissue penetration for protrusions (182). Drivers (188) may also provide lateral structural support for protrusions (182) as protrusions (182) are driven through tissue. While drivers (188) enter tissue with protrusions (182) in this example, that is not necessary in all versions. Resilient member (189) biases driver (188) back within fastener recess (172) after firing beam (160) passes driver (188), as shown in FIGS. 10B and 11B. Barbs (184) and base (186) are configured to hold fasteners (180) within tissue after receptacle (188) returns within fastener recess (172). As shown in FIG. 12, tissue layer portions (2, 4) have been thermally sealed in section (6) by electrode surfaces (150, 152). Fasteners (180) were deployed adjacent to thermally sealed section (6). The tips of protrusions (182) extend through tissue layer portions (2, 4) to provide reinforcement to the thermal seal. Base (186) of fastener (180) engages the bottom surface of tissue layer portions (2, 4) to prevent fastener (180) from advancing too far through tissue layer portions (2, 4) and to provide additional support along the length of fastener (180). Fasteners (180) provide structural support to prevent separation forces from reaching the seal created by the RF energy, such that the RF seal does not need to bear significant forces that might otherwise peel tissue layer portions (2, 4) apart.

Once fasteners (180) have been deployed from cartridge (170), end effector (140) may continue to be used with the empty cartridge (170) attached to lower jaw (142). Because cartridge (170) wraps around lower jaw (142), cartridge (170) does not interfere with the RF activity. Alternatively, cartridge (170) may be removed from end effector (140) after fasteners (180) have been deployed. Another cartridge (170) may be reloaded onto end effector (140) to deploy additional fasteners (180). This reloading may be done within the patient, without having to remove end effector (140) from the patient. For example, cartridge (170) may be exchanged via a trocar.

2. Exemplary Tissue Tacking Cartridge with a Sled

Figure 14:
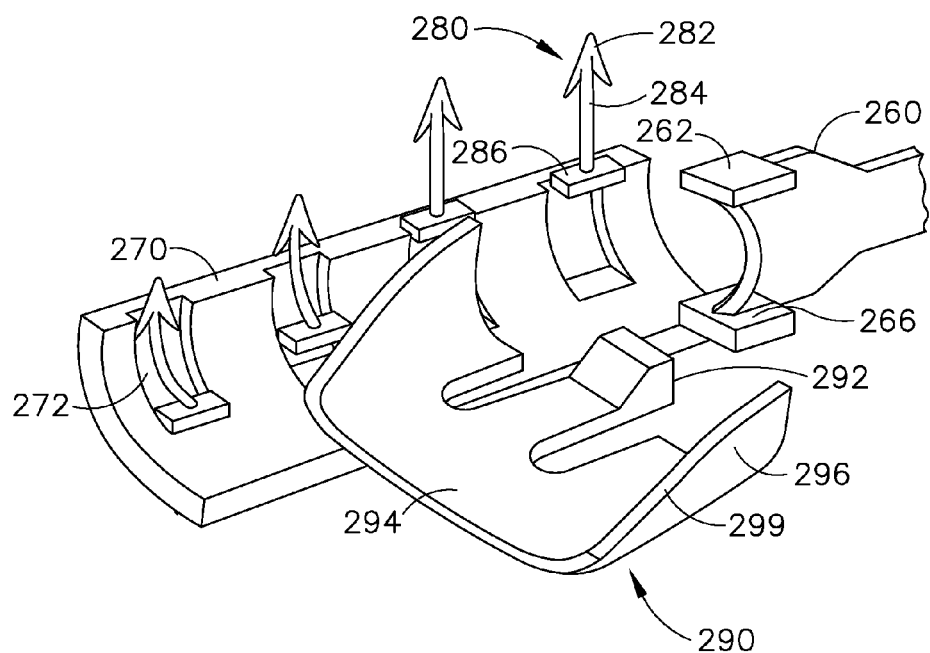
FIG. 14 depicts a partial perspective view of the tissue tacking cartridge of FIG. 13.

FIGS. 13-16 show another exemplary snap-on tissue tacking cartridge (270) for coupling with end effector (240). End effector (240) is similar to end effector (140) described above. Cartridge (270) is similar to cartridge (170), except that cartridge (270) comprises a sled (290) to deploy fasteners (280), as shown in FIG. 14. Because sled (290) is used to deploy fasteners (280), firing beam (260) of end effector (240) is similar to firing beam (60) of end effector (40). Sled (290) comprises a base (294), fastener driving cams (296) extending from base (294), and a tab (292). Fastener driving cams (296) comprise angled surfaces (299) to push fasteners (280) upward as firing beam (260) is advanced through lower jaw (242). Tab (292) extends from the back of base (294) such that lower flange (266) of firing beam (260) engages tab (292) to advance sled (290) forward as firing beam (260) advances. Tab (292) may be flexible to allow firing beam (260) to reset. For example, at the end of a firing stroke, sled (290) stops before firing beam (260). Firing beam (260) continues to advance, and tab (292) flexes downwardly to permit this and snaps up behind lower flange (266) of firing beam (260). With tab (292) snapped behind lower flange (266), sled (290) is retracted when firing beam (260) is retracted to open jaws (242, 244). At the end of a retraction stroke, sled (290) stops first again while firing beam (260) continues to be retracted. Tab (292) again flexes downwardly to decouple from lower flange (266), thereby decoupling firing beam (260) from sled (290).

Figure 15:
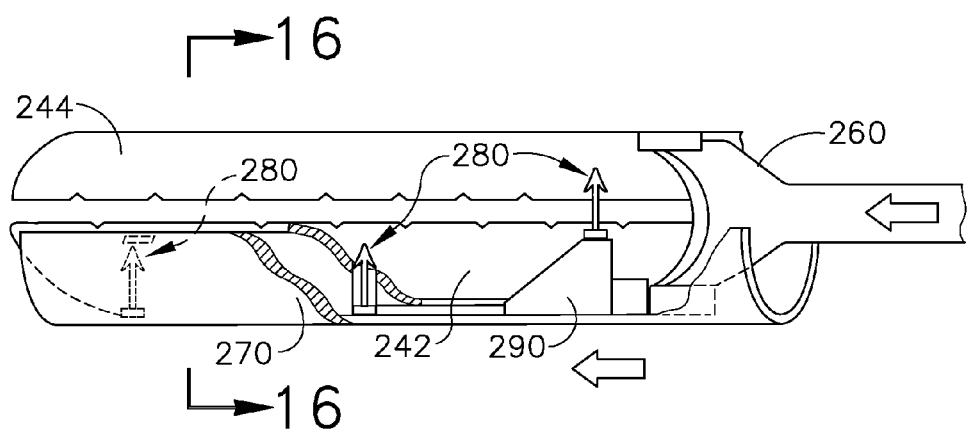
FIG. 15 depicts a partial side view of the end effector of FIG. 13, showing a firing beam advancing through the end effector.
Figure 16:
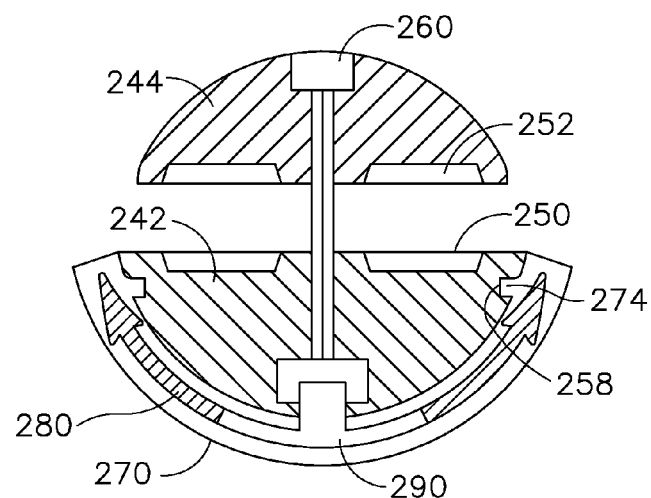
FIG. 16 depicts a cross-sectional end view of the end effector of FIG. 15 taken along line 16-16 of FIG. 15.

Fasteners (280) are stored within fastener recesses (272) of cartridge (270), as shown in FIG. 14. Fasteners (280) comprise a base (286), a protrusion (284) extending from base (286), and a pointed tip (282) transverse to protrusion (284) to form a t-tag configuration. Sled (290) directly contacts base (286) of fastener (280) to deploy fastener (280) from fastener recess (272), as shown in FIG. 15. As sled (290) is advanced by firing beam (260), angled surfaces (299) of fastener driving cams (296) contact base (286) of fastener (280) to push fastener (280) upward. Tip (282) of fastener (280) penetrates tissue to protrude transversely across the top surface of the tissue. Protrusion (284) extends through the tissue to provide structural reinforcement. Base (286) engages the bottom surface of the tissue to prevent fastener (280) from advancing too far and to hold fastener (280) in place within the tissue.

Tissue tacking cartridge (270) may be coupled to lower jaw (242) by sliding cartridge (270) upward onto lower jaw (242). The engagement between protrusions (274) of cartridge (270) and engagement recesses (258) of lower jaw (242) secures cartridge (270) to lower jaw (242). End effector (240) may then be positioned at a desired position to capture two layers of tissue between jaws (242, 244). Firing beam (260) may be advanced to close jaws (242, 244) and sever the clamped tissue layers, as shown in FIG. 15. With severed tissue layer portions being compressed between jaws (242, 244), electrode surfaces (250, 252) are activated to thermally weld the tissue layer portions together. Also while firing beam (260) advances, angled surfaces (299) on fastener driving cams (296) contact fasteners (280) to push fasteners (280) up through fastener recesses (272), as shown in FIG. 15. Fasteners (280) penetrate the tissue layer portions outside of the thermal weld zone of electrode surfaces (250, 252) to provide reinforcement in securing apposed tissue layers together. FIG. 15 shows fasteners (280) being deployed by sled (290) before firing beam (260) reaches that region. Fastener driving cams (296) could alternatively be configured to deploy fasteners (280) after firing beam (260) passes that region or be located at substantially the same longitudinal position as firing beam (260). In other words, fastener driving cams (296) may be located at a longitudinal position that is proximal to the longitudinal position of firing beam (260), such that firing beam (260) severs tissue before fastener driving cams (296) drive fasteners (280) into that same region of tissue. Alternatively, fastener driving cams (296) may be located at a longitudinal position that is proximal to the longitudinal position of firing beam (260), such that fastener driving cams (296) drive fasteners (280) into a localized tissue region that is being severed by firing beam (260) substantially simultaneously. Drivers similar to drivers (188) may be used to help guide fasteners (280) through tissue.

Once fasteners (280) have been deployed from cartridge (270), end effector (240) may continued to be used with the empty cartridge (270) attached to lower jaw (242). Alternatively, cartridge (270) may be removed from end effector (240) after fasteners (280) have been deployed. Another cartridge (270) may be reloaded onto end effector (240) to deploy additional fasteners (280).

Figure 17:
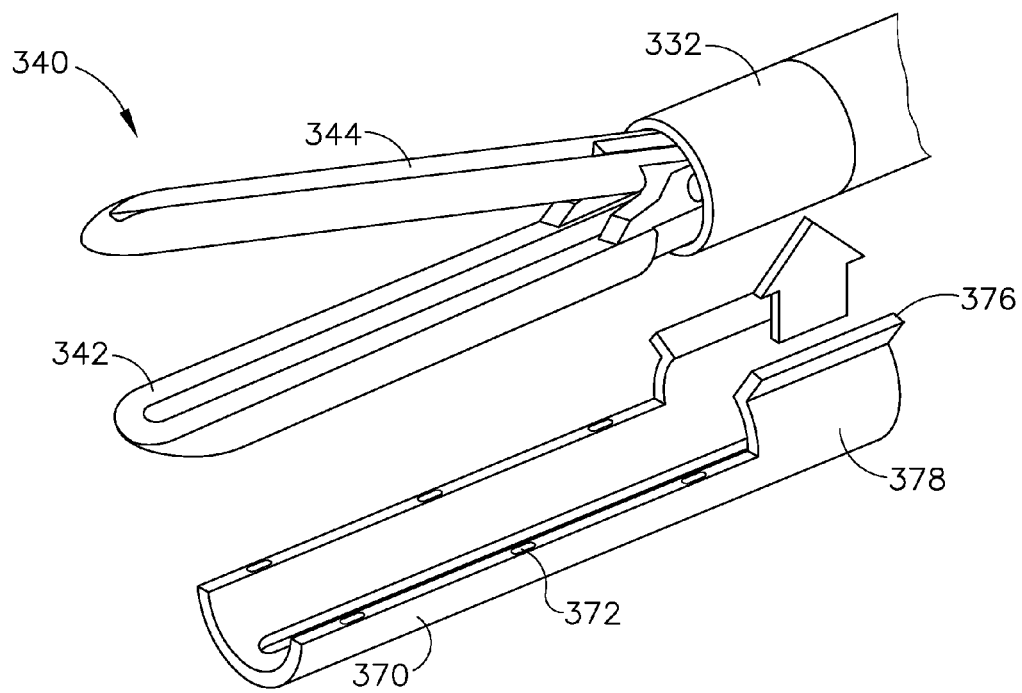
FIG. 17 depicts a perspective view of another exemplary end effector for use with the instrument of FIG. 1, showing a tissue tacking cartridge.

As shown in FIG. 17, a cartridge (370) may couple to an end effector (340) by engaging outer sheath (332) in addition to or as an alternative to snapping onto lower jaw (342). End effector (340) of this example is similar to end effector (40). Cartridge (370) is similar to cartridge (270), except that cartridge (370) comprises extensions (378) to couple to end effector (340) instead of protrusions (274). Extensions (378) are rounded inward to correspond to the rounded surface of outer sheath (332). Extensions (378) comprise angled surfaces (376) that angle outward to help guide outer sheath (332) into extensions (378). Angled surfaces (376) deflect extensions (378) outwardly as cartridge (370) is snapped onto outer sheath (332). To couple cartridge (370) to end effector (340), cartridge (370) is pushed upward onto the bottom surface of end effector (340) to engage lower jaw (342). As cartridge (370) is pushed upward, angled surfaces (376) guide outer sheath (332) into extensions (378). Extensions (378) flex outward as outer sheath (332) is inserted into extensions (378). Once outer sheath (332) is inserted within extensions (378), extensions (378) flex back inward to wrap around outer sheath (332). Extensions (378) wrap around at least a portion of the top of outer sheath (332) to prevent outer sheath (332) from sliding out of cartridge (370). To remove cartridge (370) from end effector (340), a user may push angled surfaces (376) outward to flex extensions (378) away from outer sheath (332). Outer sheath (332) may then be pulled out of extensions (378). Other suitable engagement configurations will be apparent to one with ordinary skill in the art in view of the teachings herein.

3. Exemplary Tissue Tacking Cartridge with Expanding Member

Figure 18:
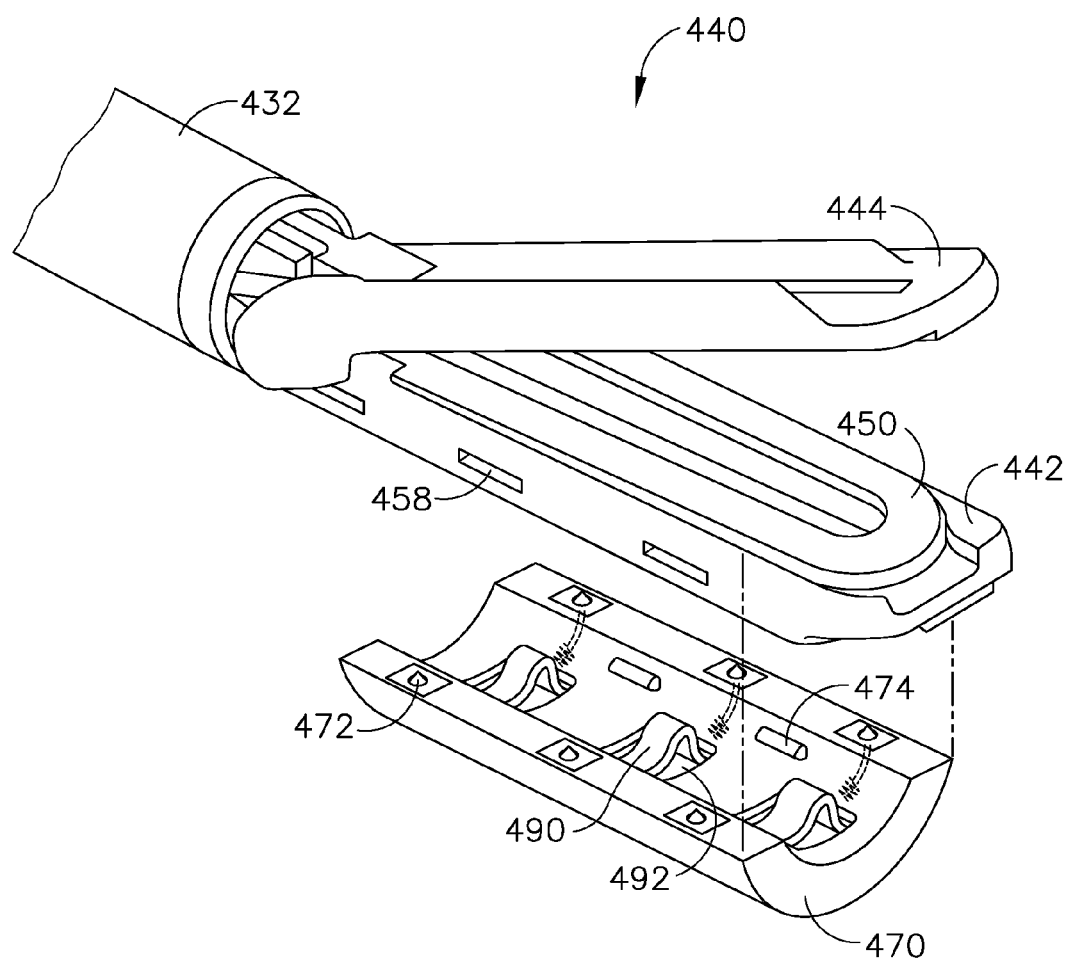
FIG. 18 depicts a perspective view of another exemplary end effector for use with the instrument of FIG. 1, showing a tissue tacking cartridge.
Figure 19A:
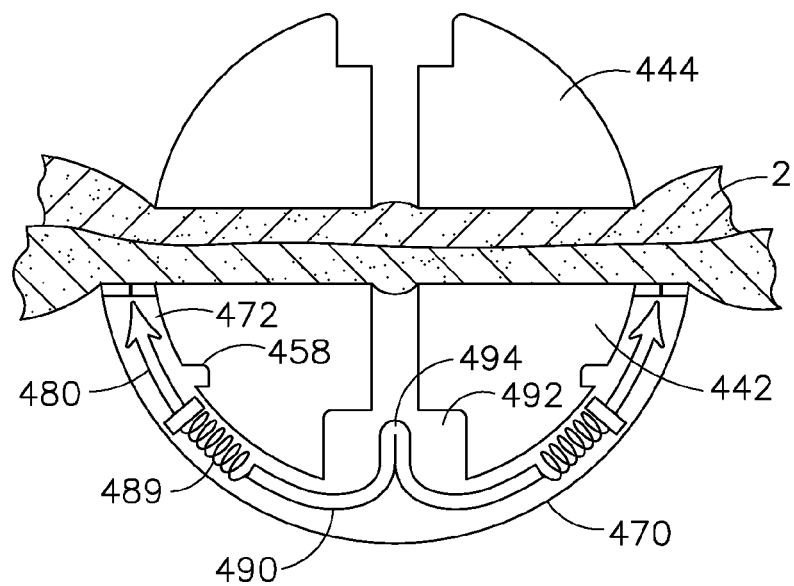
FIG. 19A depicts a cross-sectional end view of the end effector of FIG. 18, with a firing beam retracted.
Figure 19B:
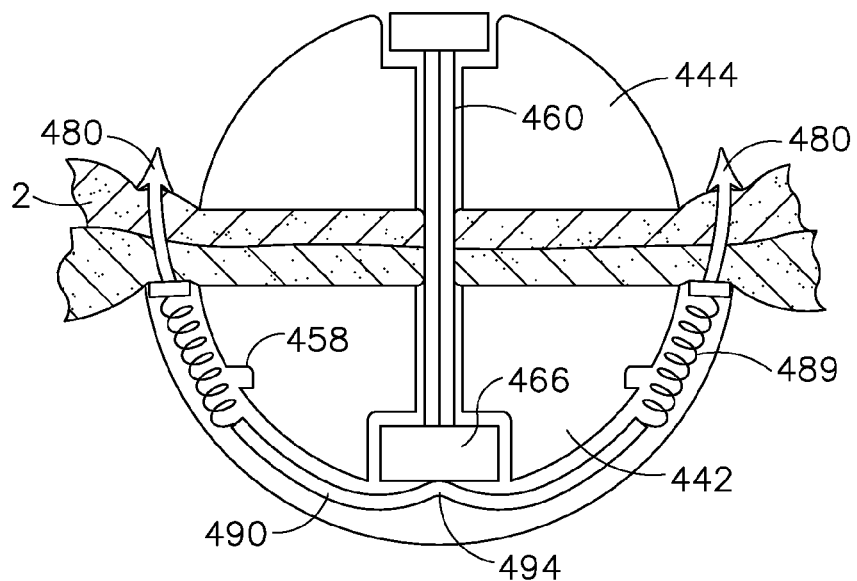
FIG. 19B depicts a cross-sectional end view of the end effector of FIG. 18, showing the firing beam advancing through the end effector.

FIGS. 18-19B show another exemplary snap-on tissue tacking cartridge (470) for coupling with end effector (440). End effector (440) is similar to end effector (240) described above. Cartridge (470) is similar to cartridge (270), except that cartridge (470) comprises expanding members (490) to deploy fasteners (480) instead of sled (290). Cartridge (470) comprises slots (492) positioned along the inner surface of cartridge (470). Expanding members (490) are bent to form a tab (494), as shown in FIG. 19A. Expanding members (490) are positioned within cartridge (470) such that tabs (494) protrude through slots (492). As firing beam (460) advances, firing beam (460) contacts tab (494) to push tab (494) down and into slot (492). This causes tab (494) to flatten and expand expanding member (490) outward to deploy fasteners (480), as shown in FIG. 19B. Fastener recesses (472) may extend through cartridge (470) such that each fastener recess (472) stores an expanding member (490) between a pair of fasteners (480). A resilient member (489) is positioned between expanding member (490) and fastener (480) to aid in deploying fastener (480) from fastener recess (472). In some versions, expanding member (490) is resiliently biased to assume the configuration shown in FIG. 19A.

Tissue tacking cartridge (470) may be coupled to lower jaw (442) by sliding cartridge (470) upward onto lower jaw (442), as shown in FIG. 18. The engagement between protrusions (474) of cartridge (470) and engagement recesses (458) of lower jaw (442) secures cartridge (470) to lower jaw (442). End effector (440) may then be positioned at a desired position to capture two layers of tissue between jaws (442, 444). Firing beam (460) may be advanced to close jaws (442, 444) and sever the clamped tissue layers. With severed tissue layer portions being compressed between jaws (442, 444), electrode surfaces (450, 452) are activated to thermally weld the tissue layer portions together. Also while firing beam (460) advances, lower flange (466) of firing beam (460) contacts tabs (494) of expanding members (490), as shown in FIG. 19B. Tabs (494) flatten within fastener recesses (472) to expand expanding member (490). When expanding member (490) expands, expanding member (490) pushes fasteners (480) up through fastener recesses (472). Resilient members (489) are biased to help deploy fasteners (480) from fastener recesses (472). Fasteners (480) penetrate the tissue layer portions outside of the thermal weld zone of electrode surfaces (450, 452) to provide reinforcement in securing apposed tissue layers together. Drivers similar to drivers (188) may be used to help guide fasteners (480) through tissue.

Figure 20A:
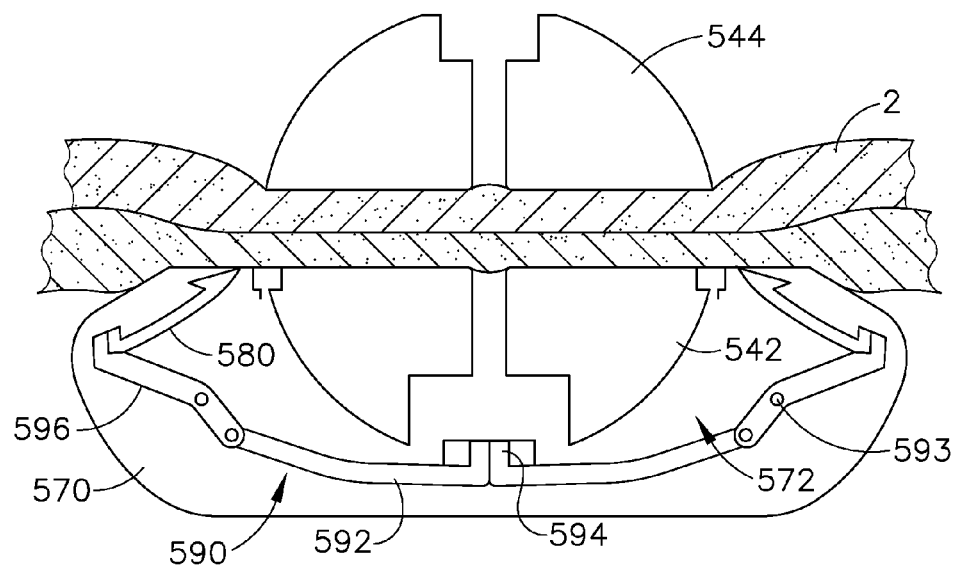
FIG. 20A depicts a cross-sectional end view of another exemplary end effector for use with the instrument of FIG. 1, showing a tissue tacking cartridge with a firing beam retracted.
Figure 20B:
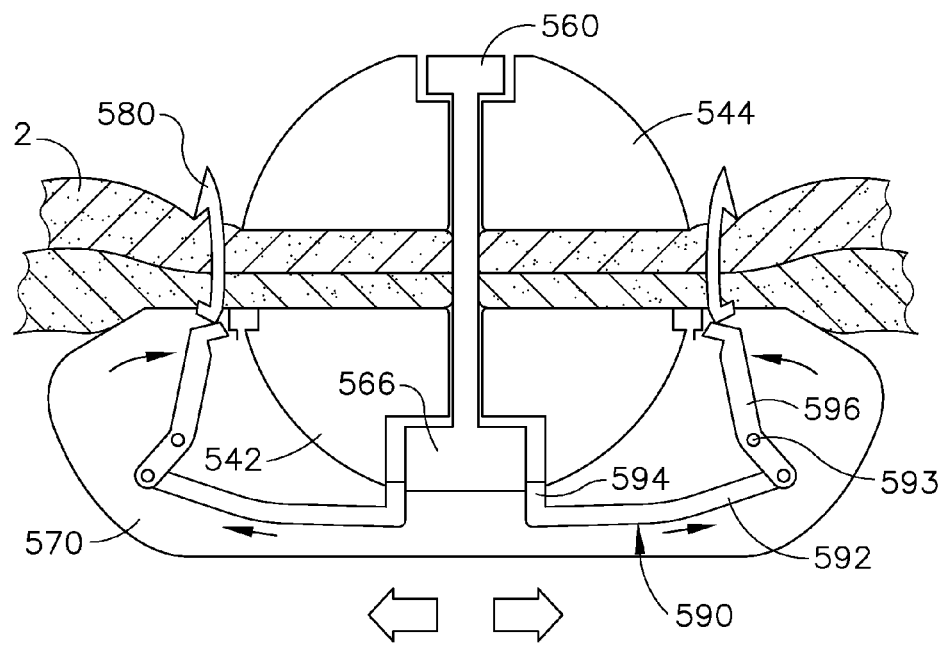
FIG. 20B depicts a cross-sectional end view of the end effector of FIG. 20A, showing the firing beam advancing through the end effector.

In some versions, as shown in FIGS. 20A-20B, firing beam (560) pushes tabs (594) of pivoting members (590) outward to deploy fasteners (580). Cartridge (570) is similar to cartridge (470), except that cartridge (570) comprises pivoting members (590) instead of expanding members (490). Pivoting members (590) each comprise a first shaft (592) and a second shaft (596) that are pivotably coupled together. Tabs (594) extend from the inner end of first shaft (592). The outer end of first shaft (592) is coupled to the inner end of second shaft (596) via pins (593). The outer end of second shaft (596) contacts fastener (580). When firing beam (560) is advanced, lower flange (566) of firing beam (560) engages tabs (594) by advancing between tabs (594) to drive tabs (594) outwardly. By way of example only, the distal end of lower flange (566) may be shaped like a plow blade with outwardly presented angled camming surfaces converging at a vertically oriented distal edge. As tabs (594) are translated outwardly by lower flange (566), first shafts (592) are also translated outwardly, as shown in FIG. 20B. This pivots second shaft (596) inwardly within fastener recess (572) to deploy fastener (580). Fasteners (580) then penetrate the tissue layer portions outside of the thermal weld zone of electrode surfaces (550, 552) to provide reinforcement.

4. Exemplary Tissue Tacking Cartridge with Sliding Member

Figure 21A:
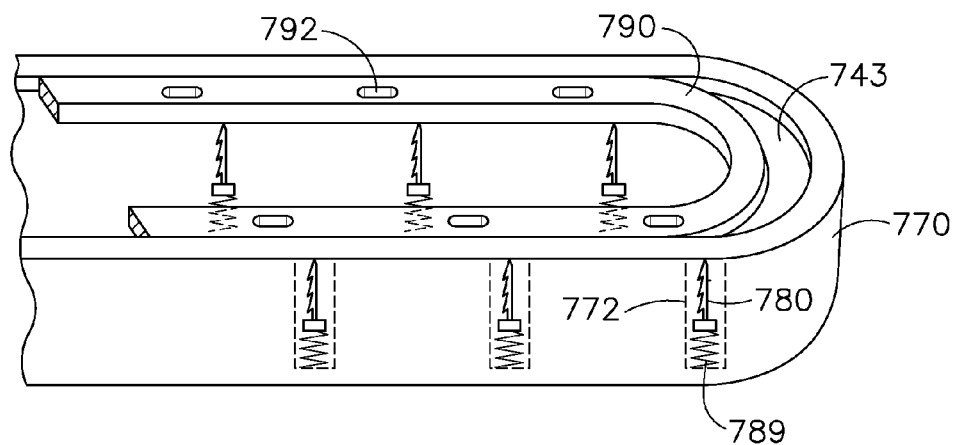
FIG. 21A depicts a partial perspective view of another exemplary tissue tacking cartridge for use with the instrument if FIG. 1, with a firing beam retracted.
Figure 21B:
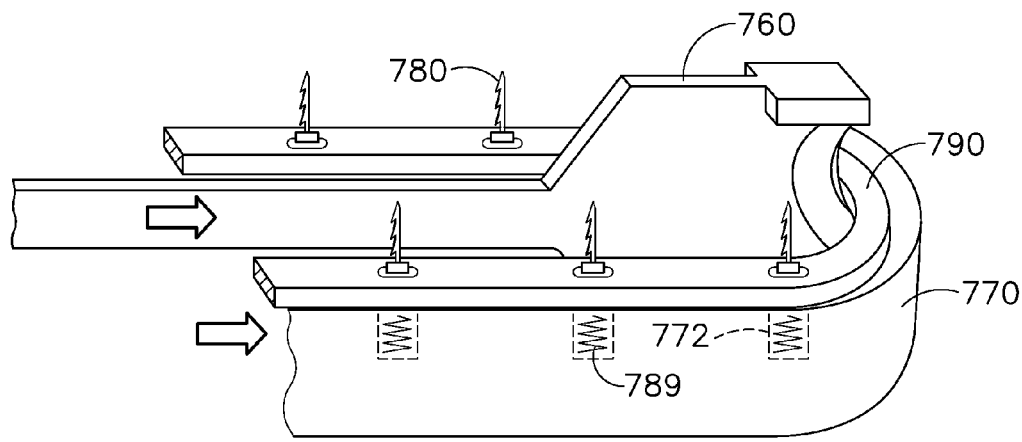
FIG. 21B depicts a partial perspective view the tissue tacking cartridge of FIG. 21A, showing a firing beam advancing through the cartridge.

FIGS. 21A-21B show another exemplary snap-on tissue tacking cartridge (770). Cartridge (770) is similar to cartridge (170), except that cartridge (770) comprises a sliding member (790) to deploy fasteners (780). Cartridge (770) comprises fastener recesses (772) to house fasteners (780) and resilient members (789). Resilient members (789) are positioned under fasteners (780) to bias fasteners (780) upward from fastener recess (772). Cartridge (770) also comprises a shelf (743) extending from the side wall of cartridge (770). Sliding member (790) is configured to slide along shelf (743). The side wall of cartridge (770) extends above shelf (743) to retain sliding member (790) within cartridge (770). The side wall of cartridge (700) may also comprise a recess on the interior of the side wall to further contain sliding member (790). A resilient member may also be positioned between the side wall and sliding member (790) to bias sliding member (790) to the proximal position. Sliding member (790) comprises a plurality of openings (792) aligned around sliding member (790). Openings (792) correspond to fastener recesses (772).

In the undeployed position, sliding member (790) rests in a proximal position on shelf (743), such that sliding member (790) covers fastener recesses (772) as shown in FIG. 21A. Resilient members (789) are compressed to push fasteners (780) against sliding member (790). When firing beam (760) advances, firing beam (760) contacts sliding member (790) to advance sliding member (790) to a distal position. In the distal position, openings (792) of sliding member (790) align with fastener recesses (772), as shown in FIG. 21B. Fasteners (780) are then free to deploy from fastener recesses (772). Resilient members (789) push fasteners (780) out of fastener recesses (772) to deploy fasteners (780). Fasteners (780) then penetrate the tissue layer portions.

B. Exemplary Tissue Tack Loading Cartridges

Fasteners (180, 280, 380, 480, 580, 780) may be provided in external tack loading cartridges that hold additional fasteners (180, 280, 380, 480, 580, 780) so that end effector (40, 140, 240, 340, 440, 540) may be reloaded with additional fasteners (180, 280, 380, 480, 580, 780) without coupling to the external tack loading cartridges. For example, an end effector (40, 140, 240, 340, 440, 540) may be placed within an external tack loading cartridge so that lower jaw (42, 142, 242, 342, 442, 542) is loaded with fasteners (180, 280, 380, 480, 580, 780). The examples below provide several versions of disposable or replaceable tissue tacking cartridges that may be readily used to load end effector (40) with fasteners (180, 280, 380, 480, 580, 780).

Figure 22A:
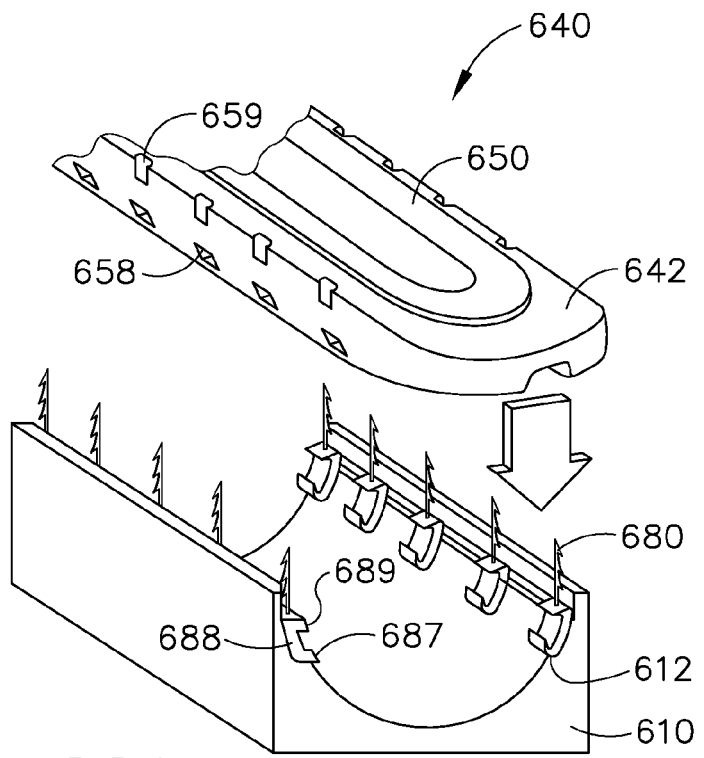
FIG. 22A depicts a partial perspective view of another exemplary end effector for use with the instrument of FIG. 1, positioned over a tissue tack loading cartridge.
Figure 22B:
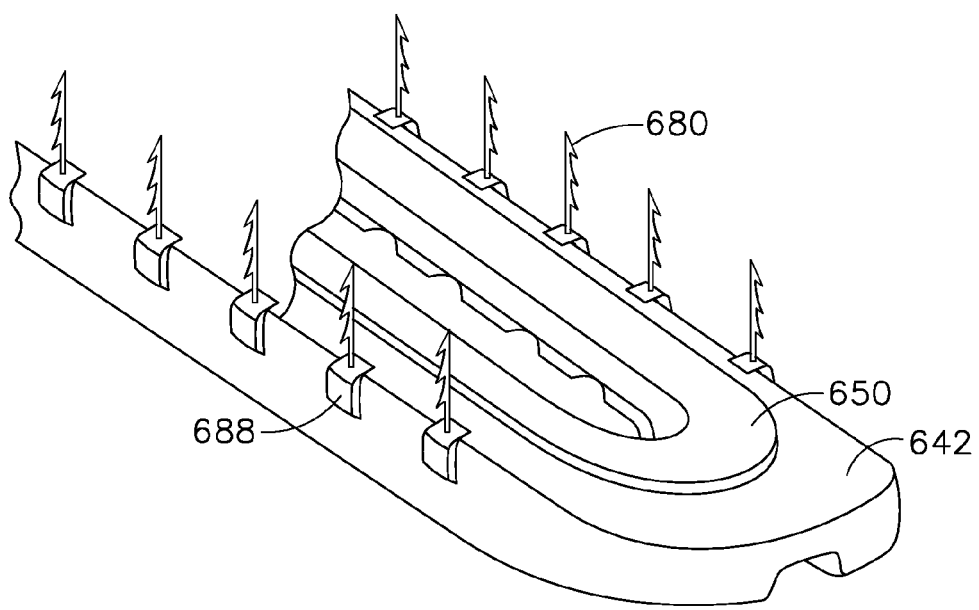
FIG. 22B depicts a partial perspective view of the end effector of FIG. 22A, showing fasteners applied to the end effector.

FIGS. 22A-22B show an exemplary external tack loading cartridge (610) to load and/or reload lower jaw (642) with fasteners (680). Lower jaw (642) is similar to lower jaw (42), except that lower jaw (642) comprises a plurality of lower engagement recesses (658) and a plurality of upper engagement recesses (659). Engagement recesses (658, 659) are positioned around the exterior of the side wall of lower jaw (642), as shown in FIG. 22A. Cartridge (610) comprises a curved inner surface with shelf (612). Shelf (612) is configured to hold a plurality of fasteners (680). Shelf (612) may be angled such that fasteners (680) are angled outward to not interfere with lower jaw (642) as lower jaw (642) enters cartridge (610). Fasteners (680) are secured to clips (688) such that fasteners (680) extend upwardly from clips (688). Clips (688) comprise an upper protrusion (689) and a lower protrusion (687). Upper protrusion (689) engages upper engagement recess (659), while lower protrusion (687) engages lower engagement recess (658) to secure fasteners (680) to lower jaw (642). Fasteners (680) are stored in cartridge (610) such that clips (688) align with engagement recesses (659, 658) when lower jaw (642) is pressed down into cartridge (610) to couple fasteners (680) to lower jaw (642).

Lower jaw (642) is then loaded with fasteners (680) by aligning lower jaw (642) over cartridge (610) such that lower jaw (642) is substantially parallel to cartridge (610) and engagement recesses (658, 659) are aligned with clips (688), as shown in FIG. 22A. Lower jaw (642) is then lowered into cartridge (610), as shown in FIG. 22B. Lower engagement recesses (658) engage lower protrusions (687) on clips (688). Shelf (612) provides a resistive force to prevent clips (688) from moving during the engagement with lower jaw (642). The contact with lower protrusions (687) then causes clips (688) to rotate upward away from shelf (612). Upper protrusions (689) flex and engage upper engagement recesses (659). This couples clips (688) with lower jaw (642) such that fasteners (680) extend upward. Lower jaw (642) may then be removed from cartridge (610).

End effector (640) may then be positioned at a desired position to capture two layers of tissue between jaws (642, 44). Firing beam (60) may be advanced to close jaws (642, 44) and sever the clamped tissue layers. With severed tissue layer portions being compressed between jaws (642, 44), electrode surfaces (650, 52) are activated to thermally weld the tissue layer portions together. As jaws (642, 44) are closed, fasteners (680) on lower jaw (642) penetrate the tissue layer portions outside of the thermal weld zone of electrode surfaces (650, 52) to provide reinforcement. When fasteners (680) are deployed into tissue, fasteners (680) may deploy from clips (688) or clips (688) may deploy with fasteners (680) into tissue. Cartridge (610) and lower jaw (642) may then be reloaded to provide additional fasteners (680).

Figure 23A:
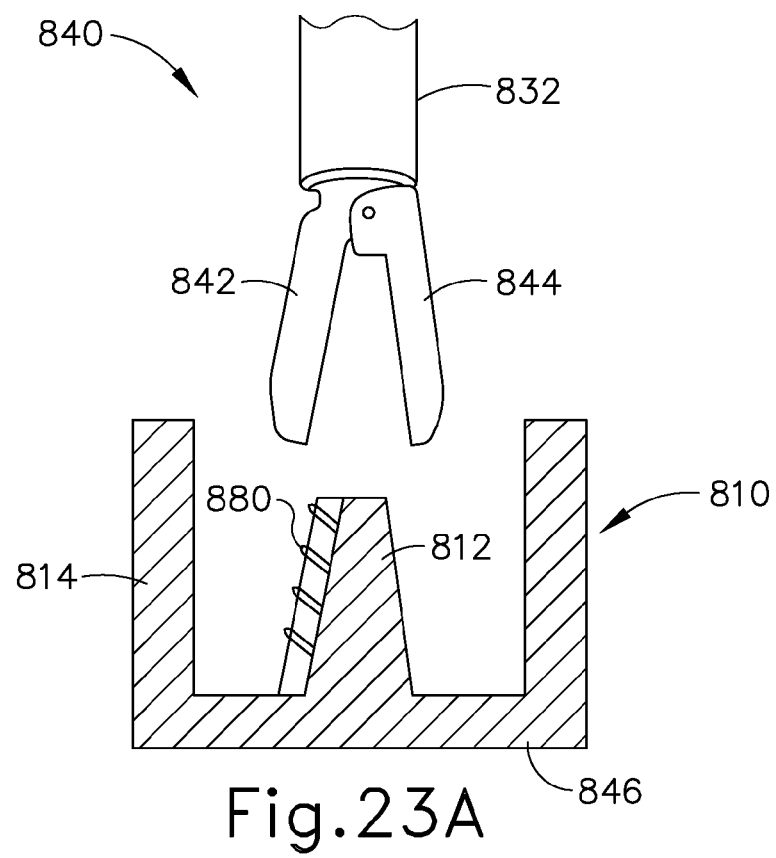
FIG. 23A depicts a partial side view of another exemplary end effector for use with the instrument of FIG. 1, positioned over another tissue tack loading cartridge.
Figure 23B:
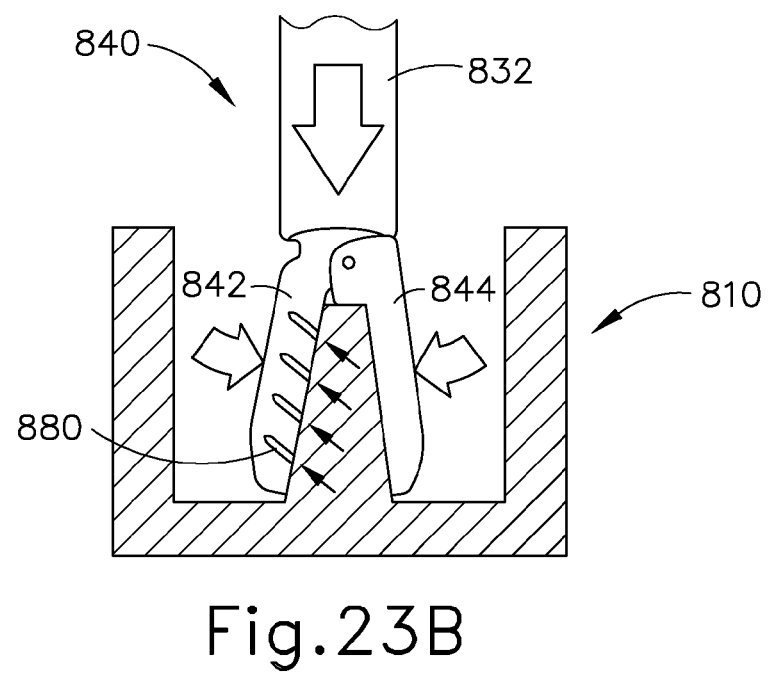
FIG. 23B depicts a partial side view of the end effector of FIG. 23A, showing the fasteners applied to the end effector.

FIGS. 23A-23B show another exemplary external tack loading cartridge (810) to load and/or reload lower jaw (842) with fasteners (880) by closing end effector (840). End effector (840) is similar to end effector (640). Cartridge (810) is similar to cartridge (610), except that cartridge (810) comprises a base (846), side walls (814), and inner wall (812). Inner wall (812) comprises a plurality of openings to house fasteners (880) and clips (888). Fasteners (880) and clips (888) are positioned within the openings such that clips (888) protrude from the openings. End effector (840) is lowered into cartridge (810) with jaws (842, 844) in the open position until engagement recesses of lower jaw (842) align with clips (888), as shown in FIG. 23A. Upper jaw (844) is closed to lower jaw (842) around inner wall (812) of cartridge (810), as shown in FIG. 23B. Clips (888) engage the engagement recesses of lower jaw (842) to secure fasteners (880) to lower jaw (842). Upper jaw (844) is then re-opened to release inner wall (812). End effector (840) may then be removed from cartridge (810) and fired as described above.

C. Exemplary Tissue Tacking Sleeve

Figure 24:
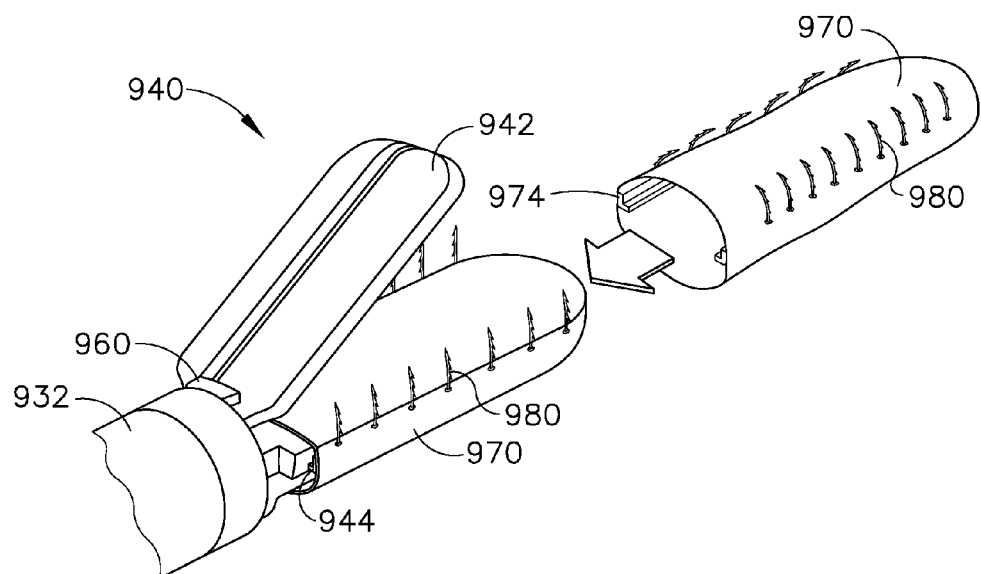
FIG. 24 depicts a perspective view of another exemplary end effector for use with the instrument of FIG. 1, showing a tissue tacking sleeve.
Figure 25:
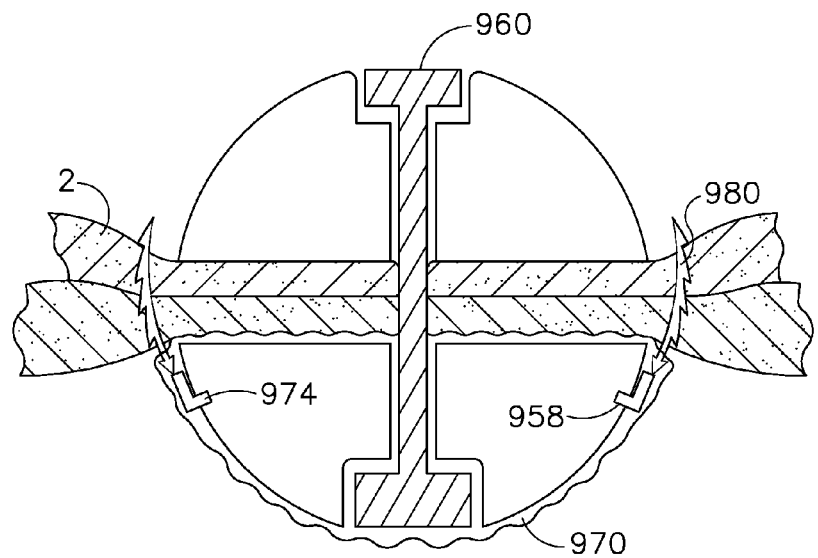
FIG. 25 depicts a cross-sectional end view of the end effector and sleeve of FIG. 24.

In some versions, a tissue tacking sleeve (970) may be provided instead of a snap-on tissue tacking cartridge (170, 270, 370, 470, 570, 770), as shown in FIGS. 24-25. End effector (940) is similar to end effector (40), except that end effector (940) further comprises an engagement recess (958) extending along each side wall of lower jaw (942). Sleeve (970) is configured to slide onto lower jaw (942), as shown in FIG. 24. Sleeve (970) comprises an alignment feature (974) extending within each side of sleeve (970). Alignment feature (974) is rigid and comprises a longitudinally L-shaped member extending through sleeve (970). Fasteners (980) extend unitarily and transversely from alignment feature (974). Sleeve (970) further comprises a plurality of openings such that fasteners (980) protrude from the openings. Before sleeve (970) is coupled to end effector (940), fasteners (980) extend inwardly from the openings of sleeve (970). Sleeve (970) is coupled to lower jaw (942) by sliding sleeve (970) onto lower jaw (942). Alignment feature (974) of sleeve (970) engages engagement recess (958) of lower jaw (942) to position sleeve (970) onto lower jaw (942) and to re-orient fasteners (980). When sleeve (970) is coupled to lower jaw (942), fasteners (980) may extend upright through the openings of sleeve (970) so that fasteners (980) are deployed into tissue when end effector (940) is closed. Sleeve (970) may comprise a non-conductive polymer to not interfere with the RF energy of end effector (940). Sleeve (970) may also be absorbable and may comprise a hemostatic agent.

With sleeve (970) coupled to end effector (940), end effector (940) may be positioned at a desired position to capture two layers of tissue between jaws (942, 944), as shown in FIG. 25. Firing beam (960) may be advanced to close jaws (942, 944) and sever the clamped tissue layers. With severed tissue layer portions being compressed between jaws (942, 944), electrode surfaces (950, 952) are activated to thermally weld the tissue layer portions together. As jaws (942, 944) are closed, fasteners (980) penetrate the tissue layer portions outside of the thermal weld zone of electrode surfaces (950, 952) to provide reinforcement. Also while firing beam (960) advances, firing beam (960) may cut the top portion of sleeve (970). The bottom portion of sleeve (970) may also be cut by firing beam (960) when firing beam (960) advances. Sleeve (970) may comprise perforations such that firing beam (960) breaks the perforations as firing beam (960) advances. Sleeve (970) is no longer coupled with end effector (940) after firing beam (960) is fired and jaws (942, 944) are opened. Sleeve (970) then remains secured to fasteners (980) and may be absorbed within the body. Another sleeve (970) may be reloaded onto lower jaw (942) to provide additional fasteners (980).

D. Exemplary Tissue Tacking Material

Figure 26:
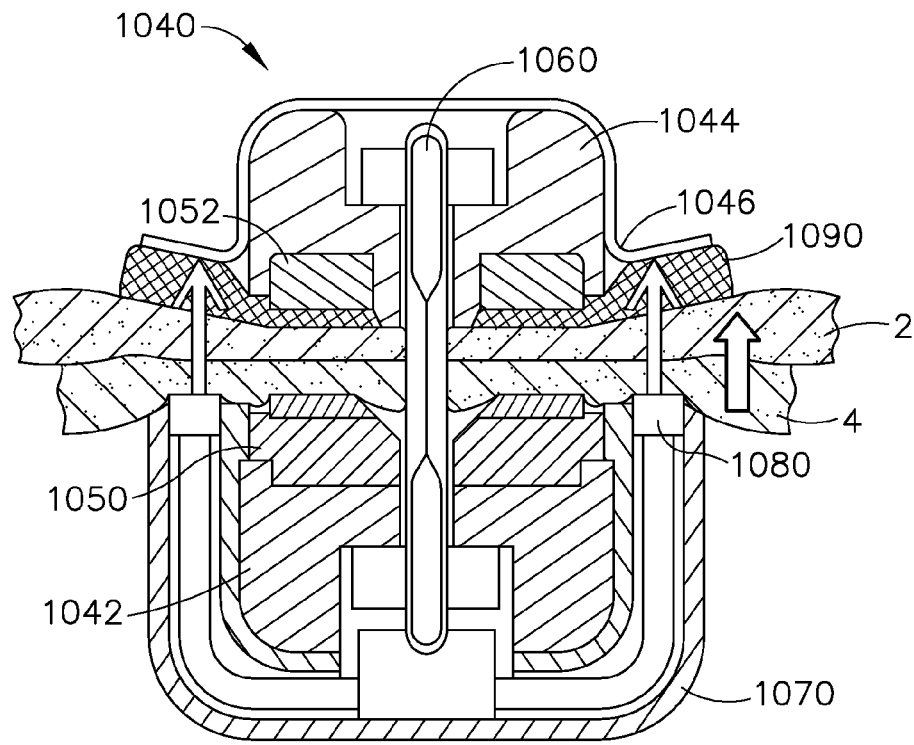
FIG. 26 depicts a cross-sectional end view of another exemplary end effector for use with the instrument of FIG. 1, showing a tissue tacking material.
Figure 27:
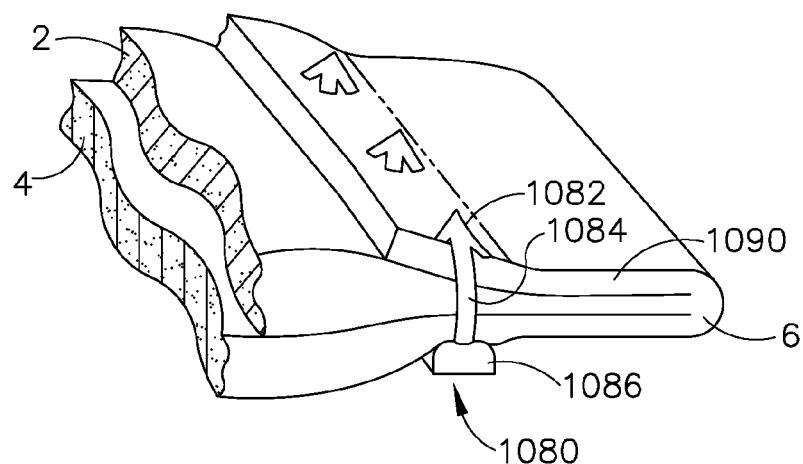
FIG. 27 depicts a perspective view of the tissue tacking material of FIG. 26 applied to tissue.

To help further protect the weld zone of electrode surfaces (1050, 1052), a tacking buttress material (1090) may be provided to divert forces that may otherwise separate RF-welded tissue layers. FIGS. 26-27 show tacking buttress material (1090) positioned between upper jaw (1044) and lower jaw (1042). An outer layer (1046) is placed over upper jaw (1044) such that outer layer (1946) extends past upper jaw (1044) to hold tacking buttress material (1090) in place. Outer layer (1046) may be adhesive so that tacking buttress material (1090) is secured to upper jaw (1044) while end effector (1040) is positioned around the tissue layer portions. End effector (1040) and cartridge (1070) may then be operated to seal and fasten the tissue layer portions. As fastener (1080) penetrates tissue (2), fastener (1080) also penetrates tacking material (1090). Tip (1082) of fastener (1080) protrudes through tacking buttress material (1090) to secure tacking buttress material (1090) with tissue (2) and remove tacking buttress material (1090) from outer layer (1046). Tacking buttress material (1090) may be formed from an absorbable material to be absorbed by the body. Tacking buttress material (1090) may be positioned either above or below tissue layer portions between jaws (1042, 1044). Tacking buttress material (1090) may be used with any of the fasteners described above.

Suitable tacking buttress materials (1090) may include but are not limited to platelet poor plasma (PPP), platelet rich plasma (PRP), starch, chitosan, alginate, fibrin, thrombin, polysaccharide, cellulose, collagen, bovine collagen, gelatin-resorcin-formalin adhesive, oxidized cellulose, mussel-based adhesive, poly (amino acid), agarose, amylose, hyaluronan, polyhydroxybutyrate (PHB), hyaluronic acid, poly(vinyl pyrrolidone) (PVP), poly(vinyl alcohol) (PVA), polylactide (PLA), polyglycolide (PGA), polycaprolactone (PCL), and their copolymers, VICRYL® (Ethicon, Inc., Somerville, N.J.), MONOCRYL material, PANACRYL (Ethicon, Inc., Somerville, N.J.), and/or any other material suitable to be mixed with biological material and introduced to a wound or defect site, including combinations of materials. For example, tacking materials (1090) may comprise a material selected from the following materials: epsilon-caprolactone glycolide, bovine pericardium, polylactic acid, polyglycolic acid, polyglactin, polydioxanone, polyglyconate, whey protein, cellulose gum, starch, gelatin, silk, nylon, polypropylene, braided polyester, polybutester, polyethylene, and/or polyetheretherketones. Other suitable compounds, materials, substances, etc., that may be used in a tacking buttress material will be apparent to those of ordinary skill in the art in view of the teachings herein.

In some versions, a medical fluid may be suspended in a biocompatible carrier to form tacking buttress material (1090). Suitable carriers may include, for example, a physiological buffer solution, a flowable gel solution, saline, and water. In the case of gel solutions, the tissue repair composition may be in a flowable gel form prior to delivery at the target site, or may form a gel and remain in place after delivery at the target site. Flowable gel solutions may comprise one or more gelling materials with or without added water, saline, or a physiological buffer solution. Suitable gelling materials include biological and synthetic materials. Exemplary gelling materials include proteins, polysaccharides, polynucleotides, and other materials such as alginate, cross-linked alginate, poly(N-isopropylacrylamide), poly(oxyalkylene), copolymers of poly(ethylene oxide)-poly(propylene oxide), poly(vinyl alcohol), polyacrylate, or monostearoyl glycerol co-Succinate/polyethylene glycol (MGSA/PEG) copolymers, and combinations of any of the foregoing.

Tacking buttress material (1090) may comprise a fibrous pad, a foam, a matrix, a mesh, or another structure, in accordance with the teachings of, by way of example, U.S. Patent App. Pub. No. 2009/0120994, entitled "Surgical Fastening Device with Initiator Impregnation of a Matrix or Buttress to Improve Adhesive Application", published May 14, 2009, now U.S. Pat. No. 7,708,180, issued May 4, 2010, the disclosure of which is incorporated by reference herein. The material may comprise, for example, a biocompatible material that is a buttress, a matrix having a plurality of openings therein, an open cell or closed cell foam, and/or a fabric pad. The material may include porosities that induce a wicking feature to drawing adhesive into the material and ensure the openings remain clear of the adhesive, allowing tissue growth through the openings after application to tissue.

Additionally or alternatively, tacking buttress material (1090) may be comprised of an adhesive such as, but not limited to, polymerizable and/or cross-linkable materials such as a cyanoacrylate adhesive. The adhesive, for example, may be a monomeric (including prepolymeric) adhesive composition, a polymeric adhesive composition, or any other compound that can adhere to tissue. In embodiments, the monomer may be a 1,1-disubstituted ethylene monomer, e.g., an alpha-cyanoacrylate. When cross linked or polymerized, the cyanoacrylate can change from a liquid to a solid. Polymerized adhesives for example, can be formulated to be flexible to rigid and could be spongy. If desired, the adhesive can be a single part or dual part adhesive, and/or can contain additives such as alternate compounds. Polymerization of the adhesive can occur from, but is not limited to, exposure to moisture, heat, and/or adhesion initiators such as those described in U.S. Patent App. Pub. No. 2009/0120994, now U.S. Pat. No. 7,708,180, the disclosure of which is incorporated by reference above. Other suitable materials and compositions that may be used to form tacking buttress material (1090) will be apparent to those of ordinary skill in the art in view of the teachings herein.

E. Exemplary Tissue Tacking Needle

Figure 28A:
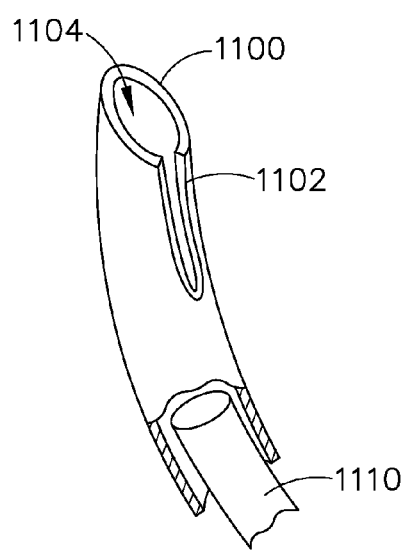
FIG. 28A depicts a perspective view of an exemplary tissue tacking needle.
Figure 28B:
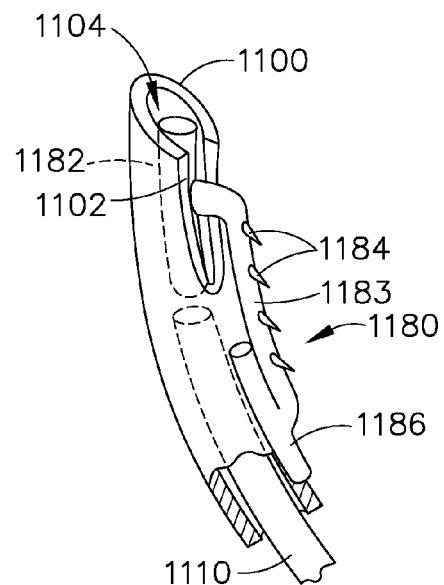
FIG. 28B depicts a perspective view of the needle of FIG. 28A loaded with a fastener.
Figure 28C:
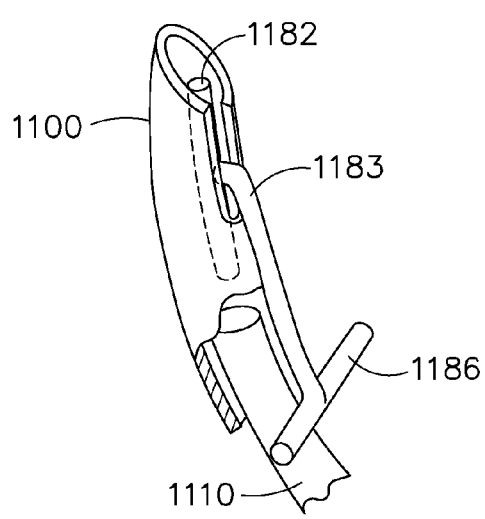
FIG. 28C depicts a perspective view of the needle of FIG. 28A, showing a wire pushing the fastener.
Figure 28D:
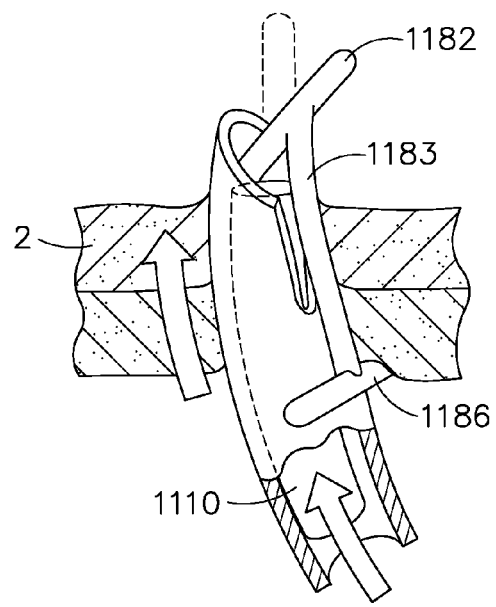
FIG. 28D depicts a perspective view of the needle of FIG. 28A, showing the fastener being applied to tissue.

Instead of using an end effector (40, 140, 240, 340, 440, 540, 640, 840, 940, 1040) to apply fasteners (180, 280, 380, 480, 580, 680, 780, 880, 980, 1080), fasteners (180, 280, 380, 480, 580, 680, 780, 880, 980, 1080) may be applied separately with a needle (1100). FIGS. 28A-28D show an exemplary tissue tacking needle (1100). Needle (1100) comprises an opening (1104) extending through needle (1100), and a slot (1102) adjacent to opening (1104) on a distal end of needle (1100), as shown in FIG. 28A. The distal end of needle (1100) is pointed to help penetrate through tissue. A fastener (1180) is positioned within the distal end of needle (1100). Fastener (1180) comprises a top portion (1182), a bottom portion (1186), and a connector (1183) extending between the top portion (1182) and bottom portion (1186). Top portion (1182) and bottom portion (1186) are transverse to connector (1183) to form an "H" configuration. Connector (1183) comprises barbs (1184) extending from connector (1183), but barbs (1184) are merely optional. Fastener (1180) is positioned within needle (1100) such that top portion (1182) is inserted within opening (1104) with connector (1183) extending from the slot (1102), as shown in FIG. 28B. A portion of connector (1183) and bottom portion (1186) remain outside of needle (1100). A wire (1110) is pushed distally through opening (1104) to push top portion (1182) of fastener (1180) out of needle (1100) to deploy fastener (1180), as shown in FIGS. 28C-28D.

An end effector (40) may be operated as described above to sever and thermally seal tissue layer portions (2). After end effector (40) is removed, needle (1100) may be inserted through the trocar. Needle (1100) may be positioned adjacent to the sealed portion of tissue (2) where reinforcement is desired. Needle (1100) may then be pushed through tissue (2) until bottom portion (1186) of fastener (1180) contacts the bottom surface of tissue (2). Wire (1110) is then pushed distally within opening (1104) to deploy top portion (1182) of fastener (1180) out of slot (1102). Top portion (1182) then rests against the top surface of tissue (2) to hold fastener (1180) in place. Needle (1100) may then be removed from tissue (2). Needle (1100) may then be reloaded with another fastener (1180) if additional reinforcement is desired. Needle (1100) and fastener (1180) may also be incorporated into an end effector (40), such that end effector (40) may include a set of needles (1100) and fasteners (1180).

III. Miscellaneous

It should be understood that any of the versions of electrosurgical instrument (10) described herein may include various other features in addition to or in lieu of those described above. By way of example only, any of the devices herein may also include one or more of the various features disclosed in any of the various references that are incorporated by reference herein.

It should also be understood that any of the devices described herein may be modified to include a motor or other electrically powered device to drive an otherwise manually moved component. Various examples of such modifications are described in U.S. Pub. No. 2012/0116379, entitled "Motor Driven Electrosurgical Device with Mechanical and Electrical Feedback," published May 10, 2012, U.S. Pat. No. 9,161,803, the disclosure of which is incorporated by reference herein. Various other suitable ways in which a motor or other electrically powered device may be incorporated into any of the devices herein will be apparent to those of ordinary skill in the art in view of the teachings herein.

It should also be understood that any of the devices described herein may be modified to contain most, if not all, of the required components within the medical device itself. More specifically, the devices described herein may be adapted to use an internal or attachable power source instead of requiring the device to be plugged into an external power source by a cable. Various examples of how medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein. Various other suitable ways in which a power source may be incorporated into any of the devices herein will be apparent to those of ordinary skill in the art in view of the teachings herein.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:
   (a) an end effector, wherein the end effector comprises:
      (i) an upper jaw, wherein the upper jaw comprises an electrode surface, and
      (ii) a lower jaw, wherein the lower jaw comprises an electrode surface corresponding with the electrode surface of the upper jaw; and
   (b) a tissue tacking cartridge, wherein the tissue tacking cartridge is coupled to one of either the upper jaw or the lower jaw, wherein the tissue tacking cartridge comprises a fastener, wherein the fastener is positioned laterally outside of the upper jaw, the lower jaw, and the electrode surfaces, wherein the fastener is operable to be deployed from the tissue tacking cartridge.

2. The apparatus of claim 1, wherein the lower jaw is fixed and the upper jaw is rotatable relative to the lower jaw, wherein the tissue tacking cartridge is coupled to the lower jaw.

3. The apparatus of claim 2, wherein the end effector comprises a firing beam, wherein the firing beam is configured to advance distally through the end effector, wherein the firing beam is operable to deploy the fastener from the tissue tacking cartridge.

4. The apparatus of claim 3, wherein the firing beam comprises fastener driving cams configured to deploy the fastener from the tissue tacking cartridge.

5. The apparatus of claim 3, wherein the end effector comprises a sled, wherein the firing beam is operable to translate the sled distally through the end effector to deploy the fastener from the tissue tacking cartridge.

6. The apparatus of claim 3, wherein the tissue tacking cartridge comprises at least one driver, wherein the driver is housed within a fastener receptacle, wherein the firing beam is operable to translate the driver to deploy the fastener from the tissue tacking cartridge.

7. The apparatus of claim 3, wherein the tissue tacking cartridge comprises at least one resilient member positioned under the fastener, wherein the at least one resilient member is biased to deploy the fastener from the tissue tacking cartridge.

8. The apparatus of claim 3, wherein the tissue tacking cartridge comprises an expanding member, wherein the firing beam is operable to expand the expanding member to deploy the fastener from the tissue tacking cartridge.

9. The apparatus of claim 3, wherein the tissue tacking cartridge comprises a pivoting member, wherein the firing beam is operable to pivot the pivoting member to deploy the fastener from the tissue tacking cartridge.

10. The apparatus of claim 3, wherein the tissue tacking cartridge comprises a sliding member, wherein the sliding member comprises at least one opening, wherein the firing beam is operable to translate the sliding member from a first position to a second position, where the sliding member is configured to cover the fastener in the first position, wherein the opening of the sliding member is configured to align with the fastener in the second position.

11. The apparatus of claim 2, wherein the lower jaw comprises a plurality of recesses, wherein the tissue tacking cartridge comprises a plurality of protrusions corresponding to the recesses, wherein the tissue tacking cartridge is configured to snap onto the lower jaw to insert the protrusions within the recesses.

12. The apparatus of claim 2, wherein the end effector comprises an outer sheath, wherein the tissue tacking cartridge comprises a pair of extensions, wherein the extensions are configured to wrap around at least a portion of the outer sheath to couple the tissue tacking cartridge with the end effector.

13. The apparatus of claim 2, wherein the tissue tacking cartridge comprises a sleeve.

14. The apparatus of claim 1, wherein the fastener comprises a base and two protrusions extending from the base, wherein the two protrusions comprise a plurality of barbs.

15. The apparatus of claim 1, wherein the fastener is absorbable.

16. The apparatus of claim 1, wherein the fastener is non-conductive.

17. The apparatus of claim 1, wherein fastener comprises a base, one protrusion extending from the base, and a top portion extending transversely from the protrusion.

18. The apparatus of claim 1 further comprising a tissue tacking buttress, wherein the fasteners are operable to penetrate the tissue tacking buttress.

19. An apparatus for operating on tissue, the apparatus comprising:
(a) an end effector, wherein the end effector comprises:
(i) an upper jaw, wherein the upper jaw comprises an electrode surface, and
(ii) a lower jaw, wherein the lower jaw comprises an electrode surface corresponding with the electrode surface of the upper jaw; and
(b) a tack loading cartridge, wherein the tack loading cartridge comprises at least one fastener, wherein the tack loading cartridge is configured to receive the end effector, wherein the tack loading cartridge is operable to load the end effector with the at least one fastener such that the at least one fastener is positioned laterally outside of the end effector and the electrode surfaces and such that the at least one fastener is operable to be deployed from the tack loading cartridge.

20. An apparatus for operating on tissue, the apparatus comprising an end effector, wherein the end effector comprises:
(a) an upper jaw, wherein the upper jaw comprises an electrode surface; and
(b) a lower jaw, wherein the lower jaw comprises an electrode surface corresponding with the electrode surface of the upper jaw, wherein the upper jaw and lower jaw are configured to transition between an open position and a closed position; and
(c) at least one fastener, wherein the at least one fastener is positioned laterally outside of the upper jaw, the lower jaw, and the electrode surfaces, wherein the at least one fastener is operable to be deployed when the upper and lower jaws are moved from the open position to the closed position.

* * * * *